United States Patent
Leo et al.

(10) Patent No.: US 11,207,341 B2
(45) Date of Patent: *Dec. 28, 2021

(54) TGF-BETA OLIGONUCLEOTIDE FOR USE IN TREATMENT OF OPHTHALMIC DISEASES

(71) Applicant: ISARNA THERAPEUTICS GmbH, Munich (DE)

(72) Inventors: Eugen Leo, Munich (DE); Michel Janicot, Munich (DE); Katja Wosikowski-Buters, Munich (DE); Petra Fettes, Munich (DE)

(73) Assignee: ISARNA THERAPEUTICS GMBH, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/348,955

(22) PCT Filed: Nov. 13, 2017

(86) PCT No.: PCT/EP2017/079032
§ 371 (c)(1),
(2) Date: May 10, 2019

(87) PCT Pub. No.: WO2018/087359
PCT Pub. Date: May 17, 2018

(65) Prior Publication Data
US 2019/0262384 A1    Aug. 29, 2019

(30) Foreign Application Priority Data

Nov. 11, 2016   (EP) .................................... 16198445

(51) Int. Cl.
| | | |
|---|---|---|
| *A61K 31/7125* | (2006.01) | |
| *A61P 27/02* | (2006.01) | |
| *A61P 41/00* | (2006.01) | |
| *A61K 31/7115* | (2006.01) | |
| *A61K 31/712* | (2006.01) | |
| *C12N 15/113* | (2010.01) | |

(52) U.S. Cl.
CPC ........ *A61K 31/7125* (2013.01); *A61K 31/712* (2013.01); *A61K 31/7115* (2013.01); *A61P 27/02* (2018.01); *A61P 41/00* (2018.01); *C12N 15/1136* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/341* (2013.01); *C12N 2310/346* (2013.01); *C12N 2320/31* (2013.01)

(58) Field of Classification Search
None
See application file for complete search history.

(56) References Cited

FOREIGN PATENT DOCUMENTS

| | | |
|---|---|---|
| WO | 2014154835 A2 | 10/2014 |
| WO | 2014154836 A2 | 10/2014 |
| WO | 2014154843 A1 | 10/2014 |

OTHER PUBLICATIONS

Stanton, R., et al.; Chemical Modification Study of Antisense Gapmers; Nucleic Acid Therapeutics, 2012, vol. 22, No. 5, pp. 344-359.

Voykrov,B., et al.; A Phase I First-in-Human single ascending dose study of iSTH0036, a potent and selective antisense oligonucleotide targeting transforming growth factor beta 1 (TGF-32) for the treatment of primary open-angle glaucoma; Presentation No. 3029-A0378.

Noh, S, et al.; Effects of ranibizumab on TGF-B1 and TGF-B2 production by human Tenon's fibroblasts: An in vitro study; Molecular Vision, 2015, vol. 21, pp. 1191-1200.

*Primary Examiner* — Tracy Vivlemore
(74) *Attorney, Agent, or Firm* — Gianna Julian-Arnold; Saul Ewing Arnstein & Lehr LLP

(57) ABSTRACT

The present invention is directed to an oligonucleotide comprising a nucleic acid sequence of SEQ ID No. 1 or parts thereof, wherein 1 to 4 nucleotides at the 3'-end and/or at the 5'-end of the oligonucleotide are modified at a base, a sugar and/or a phosphate for use in a method of reducing or inhibiting of scarring, of fibrotic closure of the trabeculectomy canal, of epithelial-to-mesenchymal transition of the trabecular meshwork and/or providing of protecting activity of the optic nerve optionally the optic nerve head. Further, the present invention refers to a pharmaceutical composition comprising such oligonucleotide and a pharmaceutically acceptable carrier.

18 Claims, 12 Drawing Sheets
Specification includes a Sequence Listing.

Fig. 1A to 1C: Downregulation of TGF-beta2 mRNA in choroid and retina (A), optic nerve (B) and lens (C)
1A)
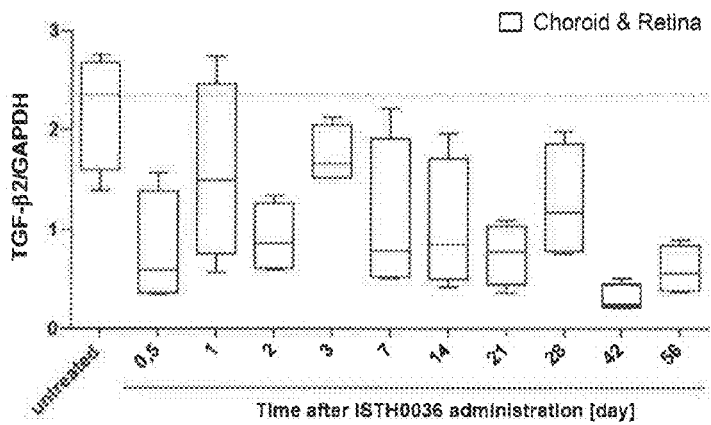
1B)
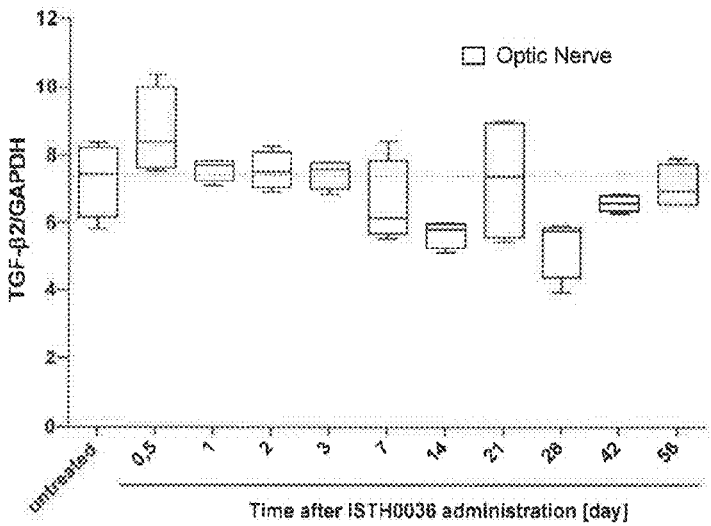
1C)
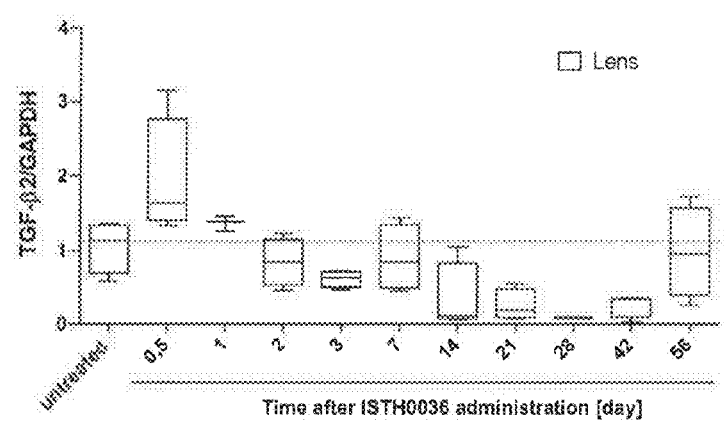

Fig. 2A and 2B: TGF-beta2 mRNA expression in retina and choroid tissues of the NZW rabbit after one or two IVT administration(s) of the TGF-beta2 antisense oligonucleotide of SEQ ID No. 2
2A)
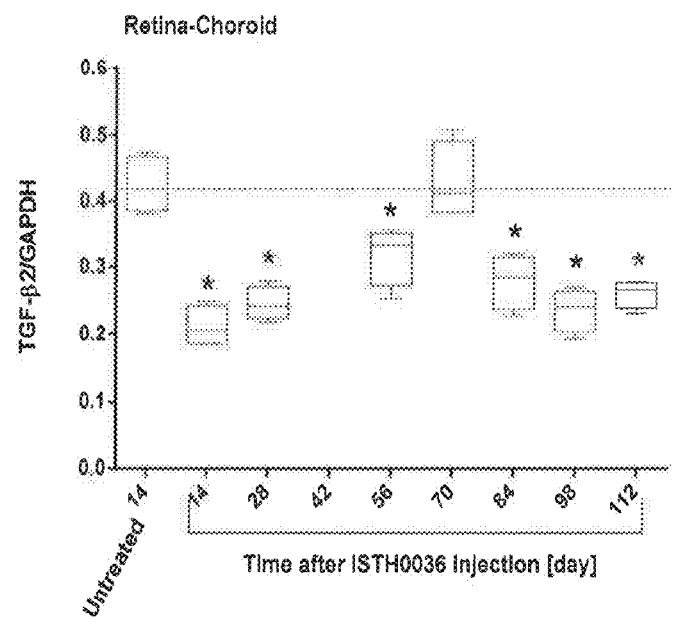
2B)
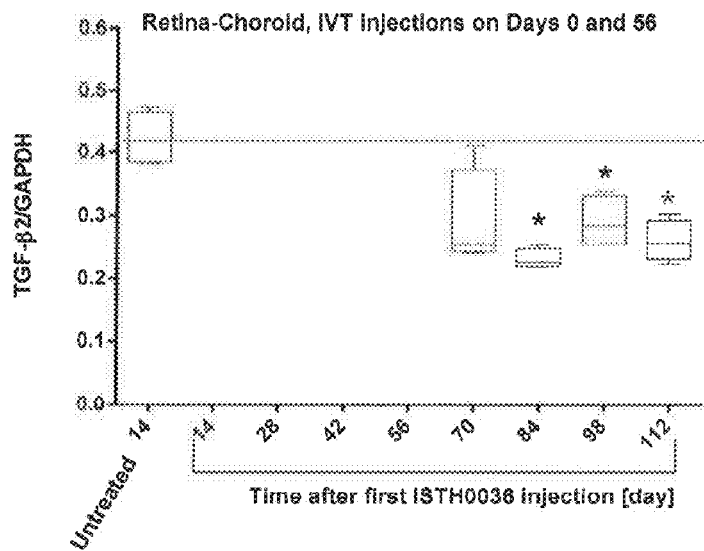

Fig. 3A and 3B: TGF-beta2 protein levels in vitreous humor of the NZW rabbit after one or two IVT administration(s) of the TGF-beta2 antisense oligonucleotide of SEQ ID No. 2
3A)
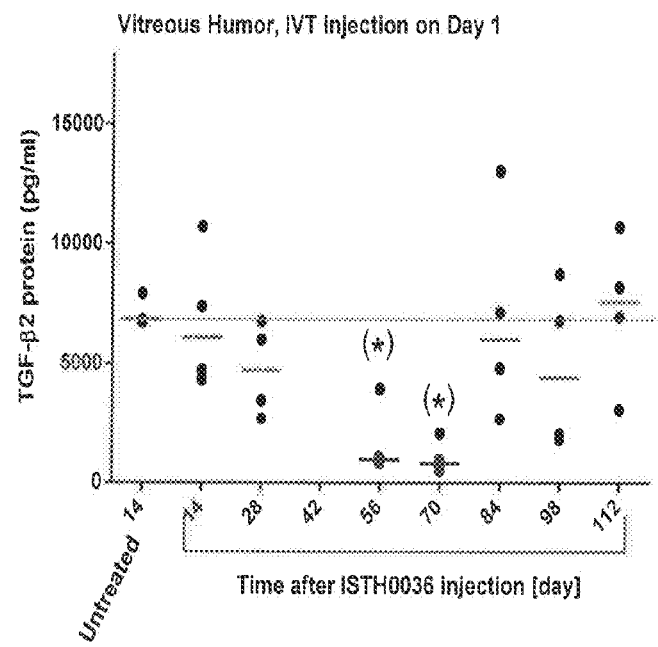
3B)

Fig. 4A and 4B: Effect of the TGF-beta2 antisense oligonucleotide of SEQ ID No. 1 on bleb size and survival in an experimental mouse glaucoma filtration surgery model
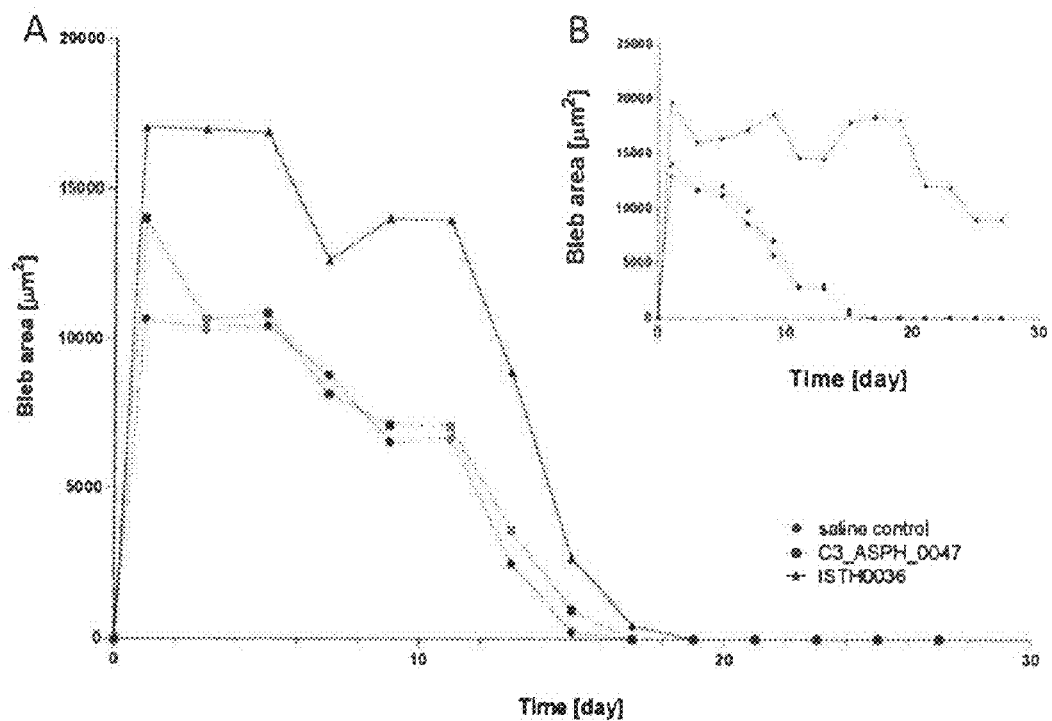
Fig. 5A and 5B: Effect of a TGF-beta2 antisense oligonucleotide of SEQ ID No. 1 on collagen deposition in the bleb area in an experimental mouse glaucoma filtration surgery model
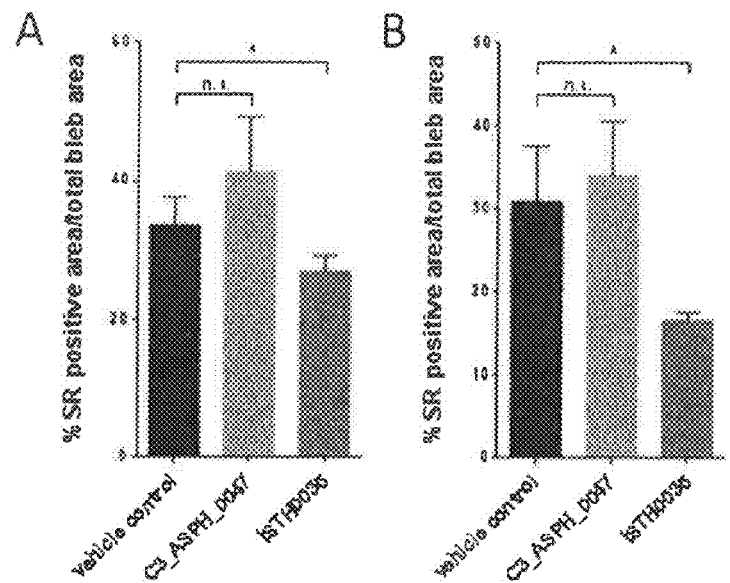

Fig. 6A to 6D: Effect of a TGF-beta2 antisense oligonucleotide of SEQ ID No. 1 on inflammation, FITC-positive area and ECM deposition in an experimental CNV mouse model
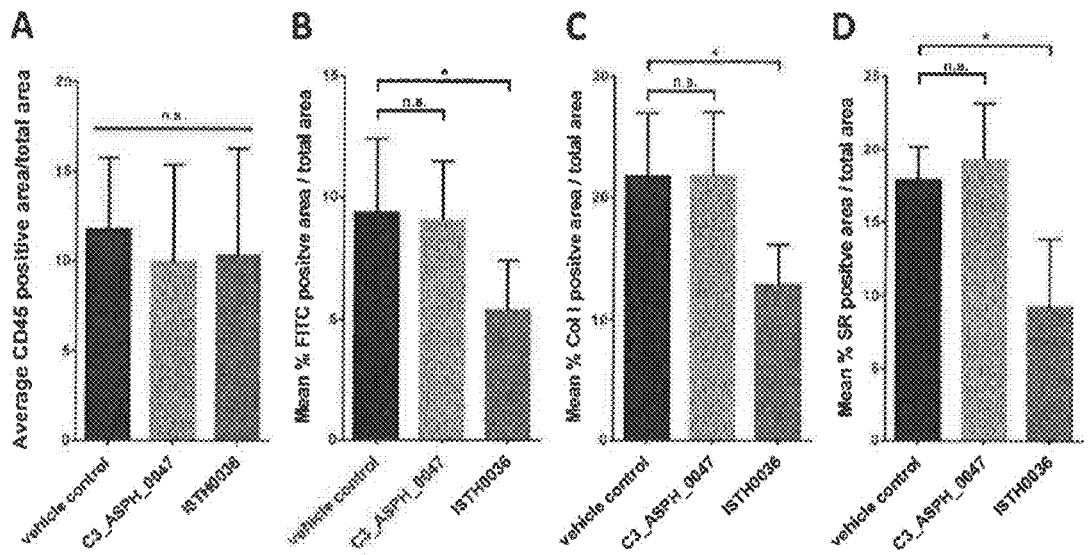
Fig. 7: Time-dependent decrease of CNV lesions induced by laser burns in mice
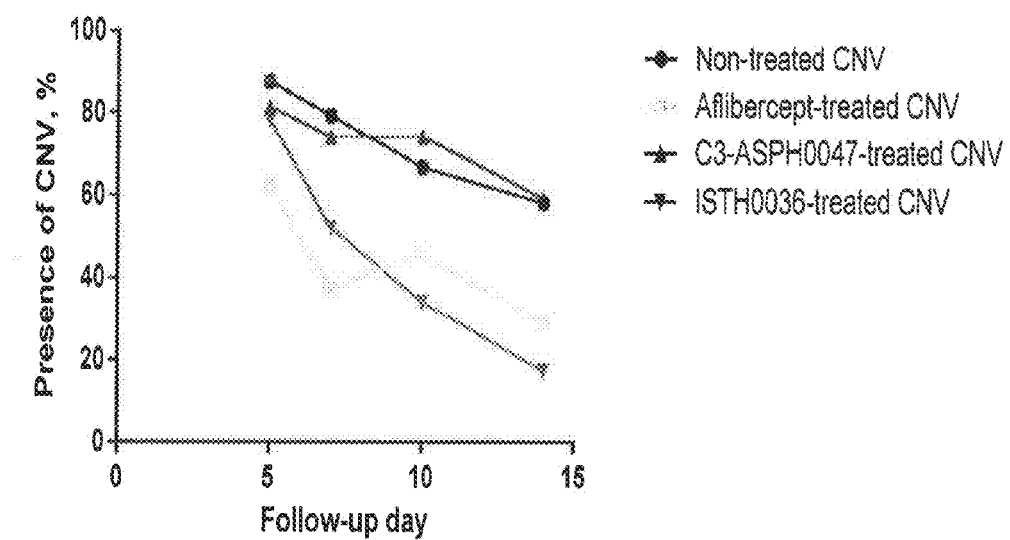

Fig. 8: Pharmacokinetic profile in vitreous humor and biodistribution in ocular tissues of New Zealand White rabbits after IVT injection of a TGF-beta2 antisense oligonucleotide of SEQ ID No. 1
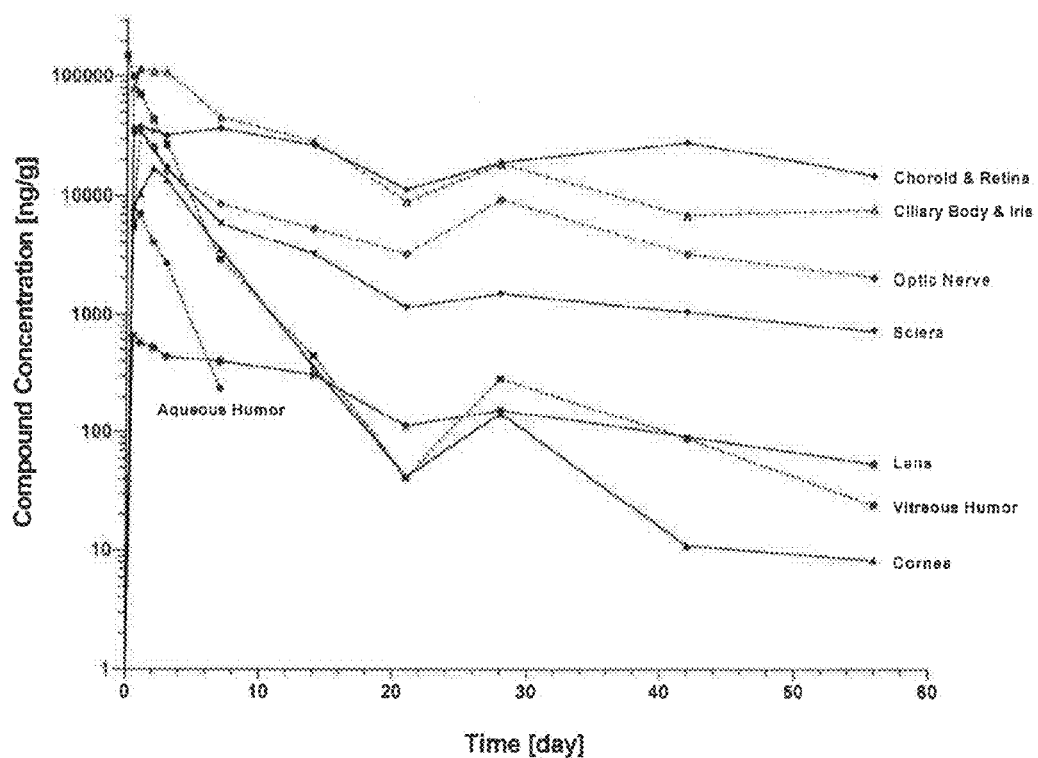

Fig. 9: Drug concentration in selected ocular tissues of NZW rabbits following one or two IVT administration(s) of a TGF-beta2 antisense oligonucleotide of SEQ ID No. 1
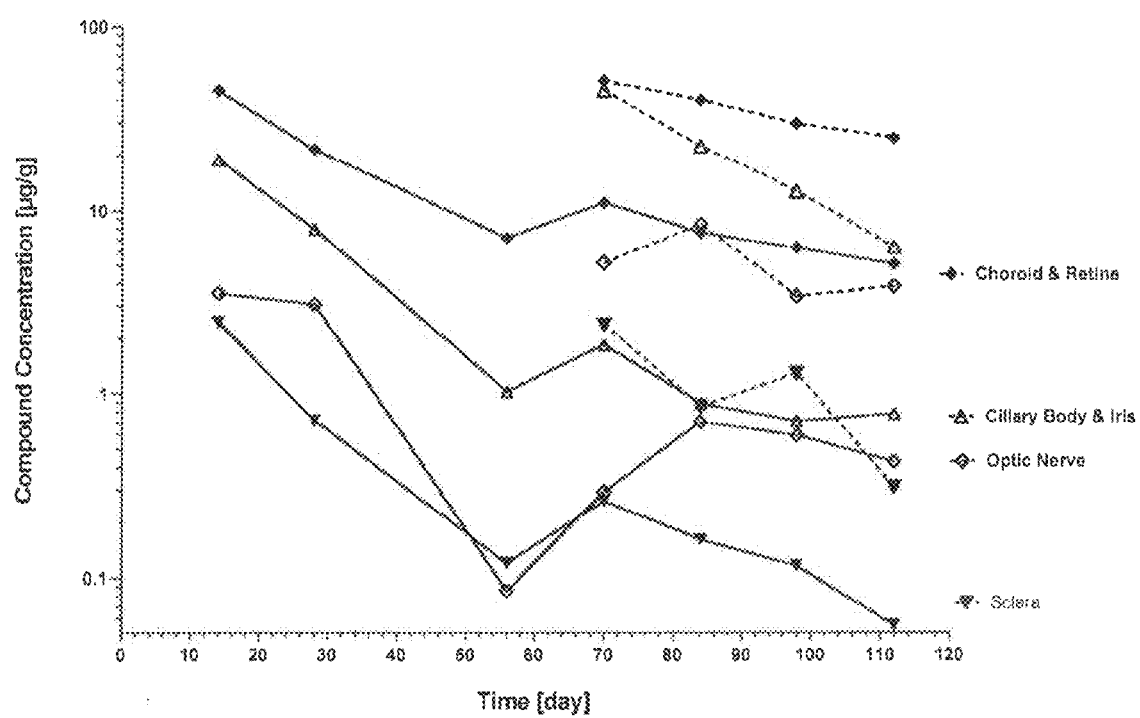

Fig. 10A and 10B: Individual IOP Course post GFS Fig. 10A) and mean IOP per Dose Level (Fig. 10B)
10A)
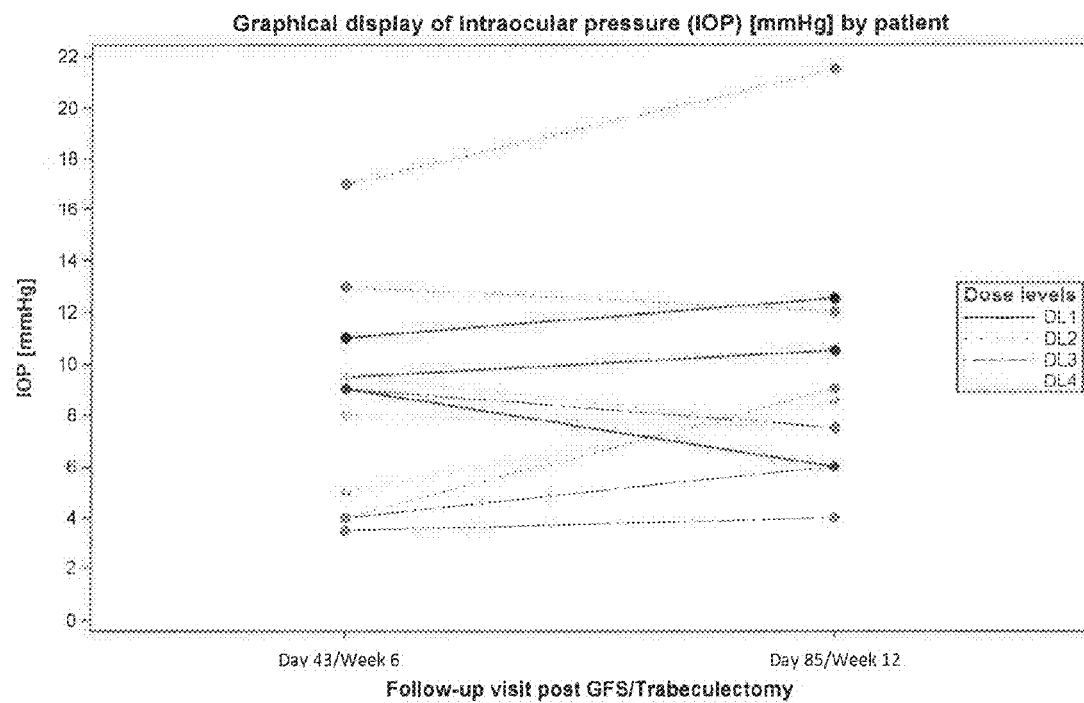
Fig. 10B:
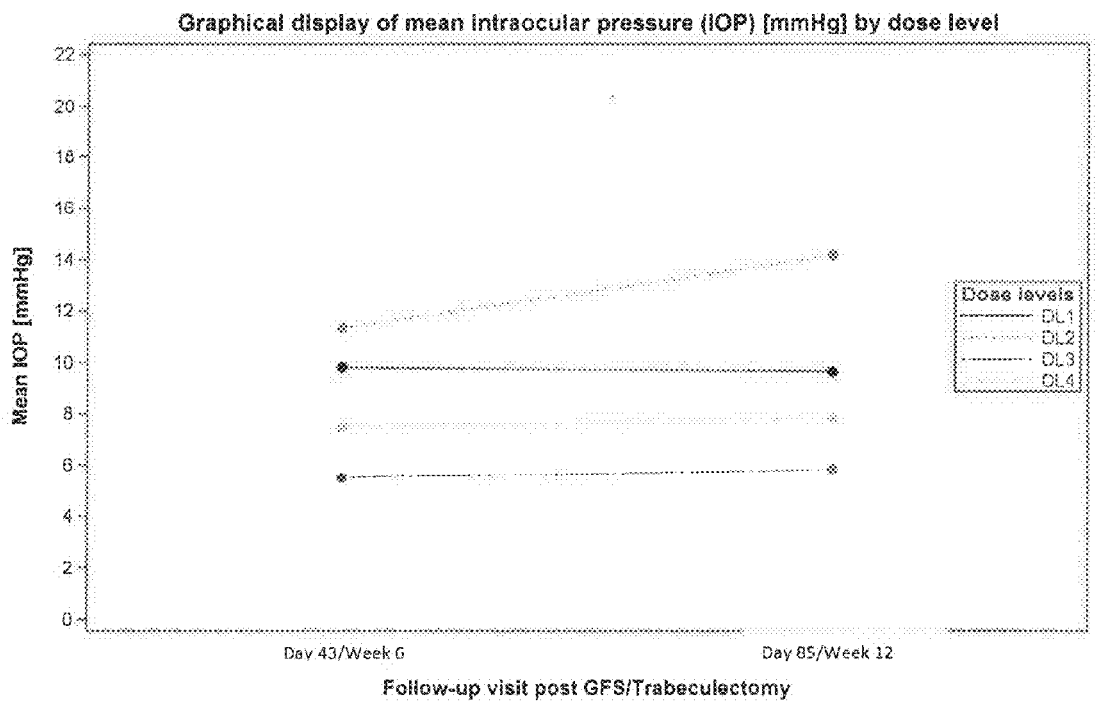

Fig. 11: Vascular leakage area corrected for presence of "0" values (37% of lowest values are excluded) and outliers. Data are expressed as mean ± SEM.
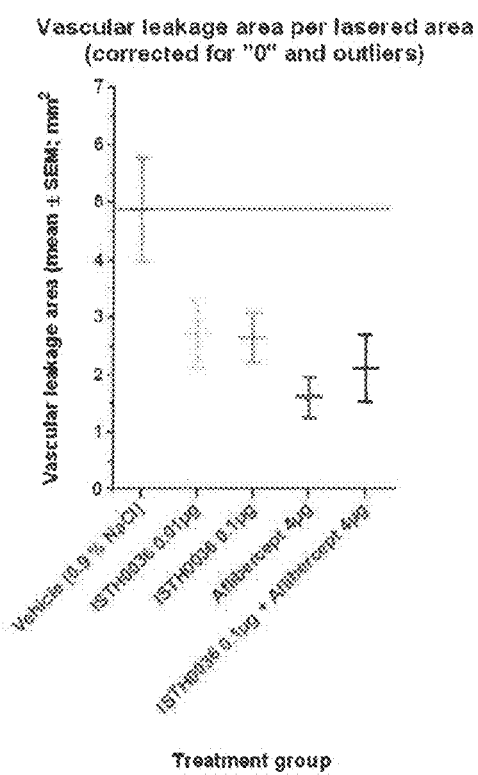

Fig. 12: ISTH0036 concentrations in ocular tissues and kidney cortex of Cynomolgus monkey following single or two IVT ISTH0036 administration(s)
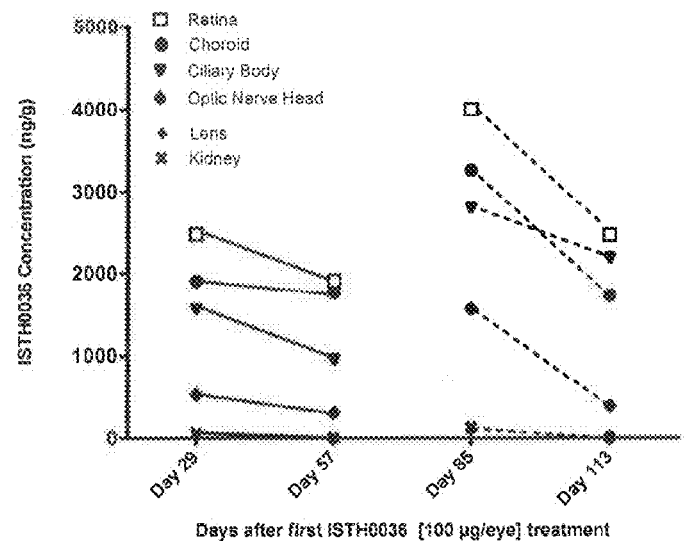
Fig. 13: Dose-dependent biodistribution of ISTH0036 in selected ocular tissues and kidney (cortex)
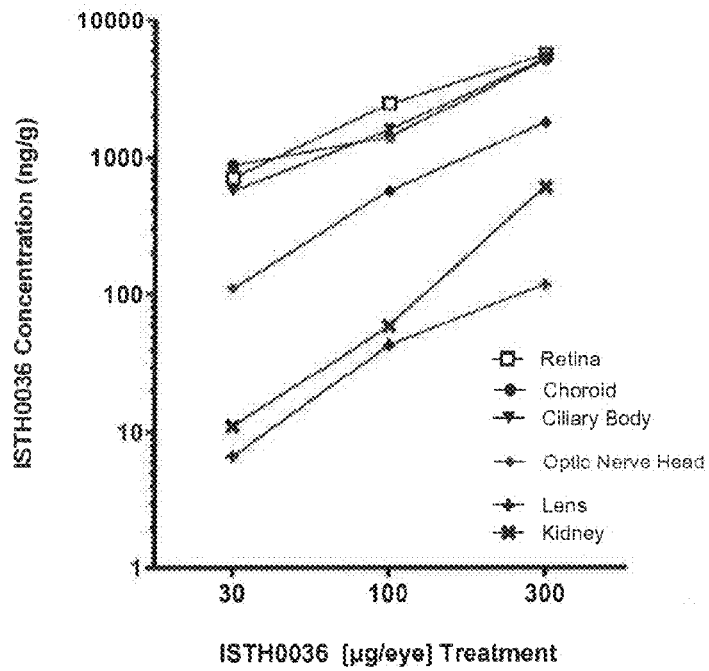

Fig. 14: Time-dependent target (TGF-beta2 mRNA) engagement in selected ocular tissues
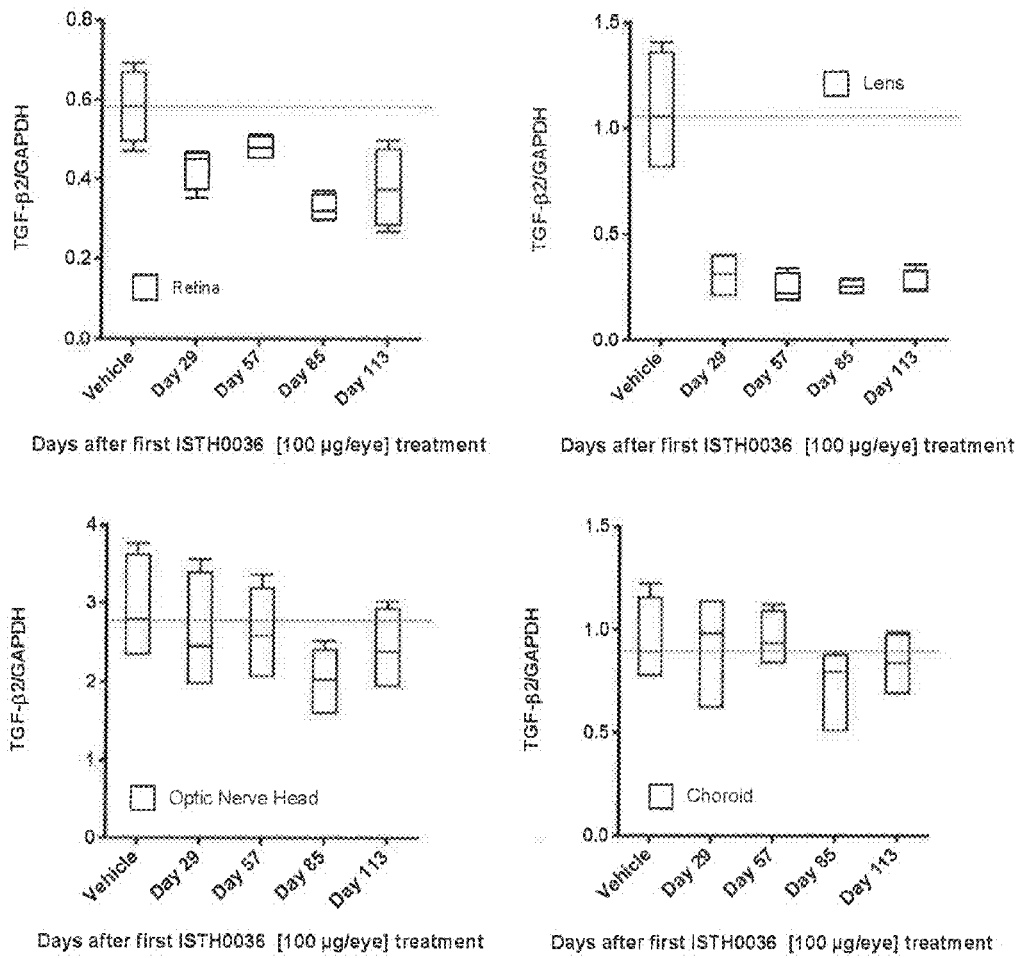
Fig. 15: TGF-beta2 mRNA expression in ocular tissues of the Cynomolgus monkey 28 days after single IVT administration of ISTH0036.
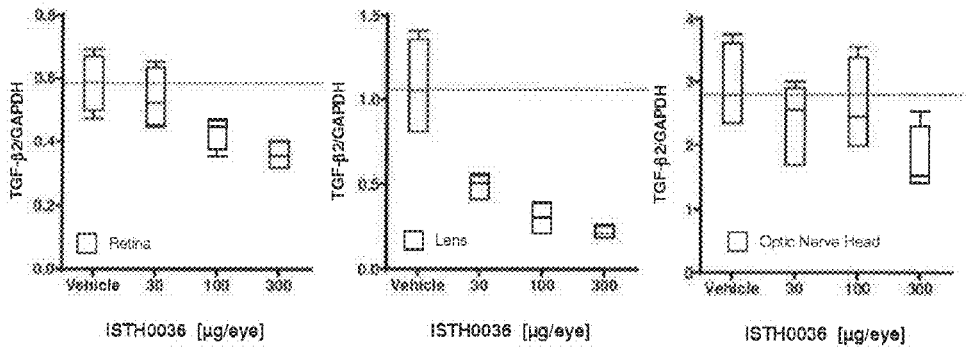

Fig. 16: TGF-beta1, -beta2 and -beta3 protein concentration in aqueous and vitreous humor
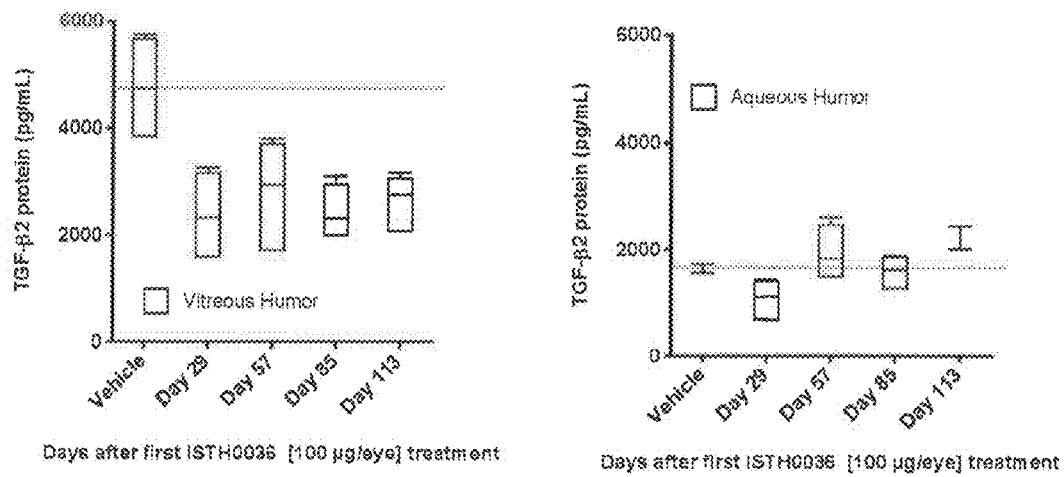
Fig 17: Individual IOP Course post GFS up to week 52
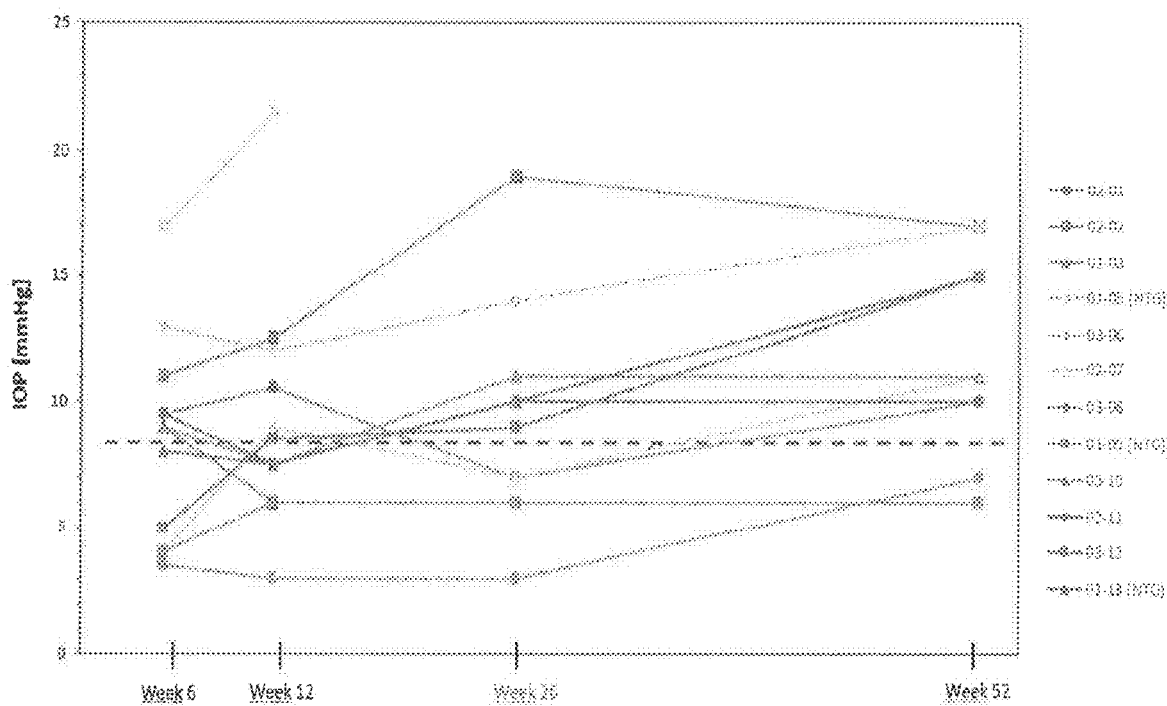

TGF-BETA OLIGONUCLEOTIDE FOR USE IN TREATMENT OF OPHTHALMIC DISEASES

CROSS REFERENCE TO RELATED APPLICATIONS

This application claims priority and the benefit of PCT/EP2017/079032, filed Nov. 13, 2017, which claims priority and the benefit of EP 16198445.5, filed Nov. 11, 2016, the entire contents of each of which are hereby incorporated in total by reference.

SEQUENCE LISTING

This application incorporates by reference the Sequence Listing contained in an ASCII text file named "362346_000SS_Sequence.txt" submitted via EFS-Web. The text file was created on May 10, 2019 and is 2 kb in size.

The present invention is directed to a TGF-beta oligonucleotide comprising a nucleic acid sequence of GACCA-GATGCAGGA or parts thereof comprising 1 to 4 modified nucleotides at the 3'-end and/or 5'-end of the oligonucleotide for use alone or in combination with an active agent in preventing and/or treating of an ophthalmic disease such as wet age-related macular degeneration (AMD), dry AMD, diabetic retinopathy (DR), diabetic macular edema (DME), choroidal neovascularization of any type, proliferative vitreoretinopathy (PVR), primary open angle glaucoma (POAG), e.g., glaucoma (hypertensive and/or normotensive), glaucoma undergoing trabeculectomy (hypertensive and/or normotensive), normotensive or hypertensive glaucoma undergoing laser-based therapy and/or corneal diseases.

TECHNICAL BACKGROUND

Antisense oligonucleotides are small single stranded oligo (deoxy)nucleotides that are complementary to a chosen sequence which can be used to prevent protein translation of certain messenger RNA by binding to them and/or to target a specific, complementary (coding or non-coding) RNA. Hence, antisense oligonucleotides have been used for decades to achieve sequence-specific silencing of gene expression. Unmodified oligonucleotides are inherently unstable in biological systems, leading to insufficient pharmacokinetic properties and suboptimal affinity to qualify as proper therapeutic drugs. Therefore, a wide range of chemical modifications have been explored and implemented over the years. Early-generation constructs (e.g., chemical modifications limited to phosphorothioate nucleotide backbone) were inactive when tested in cell-based assays unless used in the presence of a delivery vehicle. More recently, using novel additional chemical modifications, (e.g., locked nucleic acid (LNA) phosphorothioate gapmer nucleic acids), resulted not only in marked resistance to nucleases, but also in sequence-specific gene silencing at low micromolar concentrations in cell-based assays in the absence of any delivery vehicle.

On the basis of mechanism of action, two classes of antisense oligonucleotides can be discerned: (i) the RNase H-dependent oligonucleotides, which induce the degradation of mRNA; and (ii) the steric-blocker oligonucleotides, which physically prevent or inhibit the progression of splicing or the translational machinery. The majority of the antisense drugs investigated in the clinic function via an RNase H-dependent mechanism. RNase H is an ubiquitous enzyme that hydrolyzes the RNA strand of an RNA/DNA duplex (Stein and Hausen, 1969). Oligonucleotide-assisted RNase H-dependent reduction of targeted RNA expression can be quite efficient, reaching 80-95% downregulation of protein and mRNA expression. In general, oligonucleotides that cannot invoke RNase H pathways are 10- to 100-fold less potent than RNase H-activating oligonucleotides of identical sequence. Furthermore, in contrast to the steric-blocker oligonucleotides, RNase H-dependent oligonucleotides can inhibit protein expression when targeted to virtually any region of the targeted mRNA.

Transforming growth factor beta (TGF-beta) is a member of a large superfamily of secreted proteins that include the three bonafide TGF-beta isoforms (TGF-beta1, -beta2 and -beta3), activins, Bone Morphogenetic Proteins (BMPs), inhibins, nodal, and others. Encoded by different genes, TGF-beta superfamily ligands are initially translated as precursor proteins with a large amino-terminal prodomain that is required for proper folding, and a more highly conserved carboxy-terminal region, which comprises the active ligand (Hinck and O'Connor-McCourt, 2011; Jenkins, 2007; Kitisin et al., 2007). At the cellular level, members of the TGF-beta superfamily regulate fundamental cell processes such as proliferation, differentiation, death, cytoskeletal organization, adhesion, and migration. Consistent with these diverse activities, the ligands play a fundamental role in virtually all processes during the development of multicellular organisms. Given this widespread activity, it is not surprising that disruptions in TGF-beta family (TGF-beta1, -beta2 and -beta3 isoforms) member-dependent signaling are detrimental to human health. Indeed, mutations or alterations in pathway components have been associated with a wide range of human diseases such as cancer, ocular diseases and various skeletal, autoimmune, cardiovascular, muscle, and fibrotic disorders (Akhurst and Hata, 2012; Massague, 2012; Moustakas and Miyazawa, 2013).

TGF-beta2 is a predominant cytokine in the eye (Freedman and Iserovich, 2013; Saika, 2006) and is found in substantial amounts in the aqueous and vitreous humors, the neuronal retina and the retinal pigmented epithelium in the healthy eye (Granstein et al., 1990; Jampel et al., 1990; Pfeffer et al., 1994). In trabecular meshwork and optic nerve head, TGF-beta2 is also present, but only expressed in small amounts; Tovar-Vidales et al., 2011). Various studies have shown the potential significance of TGF-beta2 signaling by observing that active TGF-beta2 protein is significantly increased intraocularly in primary open-angle glaucoma (POAG) patients (Inatani et al., 2001; Min et al., 2006; Ochiai and Ochiai, 2002; Ozcan et al., 2004; Picht et al., 2001; Schlotzer-Schrehardt et al., 2001; Tripathi et al., 1994; Trivedi et al., 2011; Yamamoto et al., 2005). TGF-beta2 protein present in the aqueous humor is released by the epithelial layers of ciliary body and lens (Allen et al., 1998; Gordon-Thomson et al., 1998; Helbig et al., 1991; Wallentin et al., 1998). Other tissues in the posterior part of the eye also produce TGF-beta2, such as retinal cells and hyaluronic cells. TGF-beta2-induced changes might contribute to deformation of the optic nerve axons by causing impairment of axonal transport and neurotrophic supply, leading to their permanent degeneration. The increase in intraocular pressure further adds mechanical stress and strain to optic nerve axons and accelerates degenerative changes (Quigley, 2011) resulting in loss of visual field.

TGF-beta also plays a distinct driving role in fibrotic diseases (Border and Noble, 1994) and epithelial-mesenchymal transition and is therefore made responsible for the increase of extracellular matrix (ECM) and cellular transformation which is reported for the trabecular meshwork in glaucoma patients (Rohen and Witmer, 1972; Tektas and Lütjen-Drecoll, 2009).

Glaucoma, the second leading cause for blindness in adults in the Western world, is a progressive optic neuropathy characterized by gradually increasing loss of retinal ganglion cells, which manifests clinically with loss of optic disc neuroretinal rim tissue, defects in the retinal nerve fiber layer, and deficits in functional visual field testing (Danesh-Meyer et al., 2006). Glaucoma is considered to be caused mainly by chronically increasing intraocular pressure. The disease is characterized by tissue-remodeling of the trabecular meshwork (via epithelial-to-mesenchymal transition (EMT)), and results amongst others in increased intraocular pressure (IOP). The IOP leads to optic nerve head damage, retinal ganglion cell death and progressive visual field loss. Despite a multitude of treatment options, including surgical procedures in refractory patients, blindness remains a major threat. Worldwide in the year 2020 the number of people with primary open-angle glaucoma (POAG) is estimated at nearly 59 million, with 5.9 million experiencing bilateral blindness (Quigley and Broman, 2006). Primary open-angle glaucoma which accounts for the majority of glaucoma cases (~90%) mainly results from impaired drainage of aqueous humor out of the eye via the trabecular meshwork and/or uveoscleral pathways (Congdon et al., 1992). The currently available treatment modalities are mainly focusing on reduction of intraocular pressure (Damiano et al., 2007) by targeting the physiologic aqueous humor dynamics. The medical armamentarium includes prostaglandin analogs, beta blockers, alpha-agonists, carbonic anhydrase inhibitors, miotics and hyperosmotics (Sambhara and Aref, 2014). Yet, many patients become refractory to the existing medications, experience increasing intraocular pressure despite all medication received, or experience adverse events related to certain medications that do not allow their use anymore.

When target intraocular pressure (Damiano et al., 2007) can no longer be achieved by medical intervention, laser or incisional surgical interventions may be indicated. Among conventional external filtering operations for glaucoma, trabeculectomy is the most commonly performed surgical intervention and remains the standard of care for patients who have failed maximal tolerated medical therapy (Bettin and Di Matteo, 2013). With this surgical technique, an artificial canal is created between the anterior chamber and the subconjunctival space, with removal of parts of the trabecular meshwork. The main threat to post-surgical failure is excessive wound healing of the conjunctiva and Tenon's capsule and scarring, processes in which TGF-beta is known to play a major role (Georgoulas et al., 2008). Subconjunctival fibrosis and the underlying mechanism of myofibroblast transformation are triggered by vascular endothelial growth factor (VEGF) which induces TGF-beta1 expression (Park et al., 2013). Anti-scarring agents have therefore found their way into clinical practice, even though most of their use is off-label. Even though these antimitotics, 5-fluorouracil (5-FU) and mitomycin C (MMC), have improved surgical success by improving bleb survival to some degree, they can potentially bring along severe vision-impairing side effects such as corneal toxicity, blebitis, endophthalmitis and hypotony (Van Bergen et al., 2014), (Lockwood et al., 2013).

Consequently, it is essential to (1) create novel treatment opportunities for patients that do no longer benefit from available standard medication and (2) improve the treatment situation of those patients that undergo trabeculectomy and/or laser-based therapy, by providing novel treatments that preserve the benefit of the surgical intervention. TGF-beta oligonucleotides of the present invention provide such treatment alternatives. They reduce or avoid (1) bleb closure post trabeculectomy by reducing or inhibiting scarring, (2) trabecular meshwork alterations by epithelial-to-mesenchymal transition resulting in tissue stiffening and consequent rise of intraocular pressure, and (3) optic nerve damage. All three processes represent key pathophysiologic steps in glaucoma progression and unwelcome post-trabeculectomy alterations.

SUMMARY

The present invention refers to an oligonucleotide comprising or consisting of a nucleic acid sequence of SEQ ID No. 1 (GACCAGATGCAGGA) or parts thereof, wherein 1 to 4 nucleotides at the 3'-end and/or at the 5'-end of the oligonucleotide are modified at a base, a sugar and/or a phosphate for use in a method of reducing or inhibiting of scarring, of fibrotic closure of the trabeculectomy canal, of epithelial-to-mesenchymal transition of the trabecular meshwork and/or providing of protecting activity to the optic nerve optionally the optic nerve head. The oligonucleotide is either used alone or in combination with an active agent such as a cytostatic, an anti-VEGF agent and/or an antifibrotic agent.

The modified nucleotides are for example selected from the group consisting of LNA, ENA; polyalkylene oxide-, 2'-fluoro-, 2'-O-methoxy-, and 2'-O-methyl-modified nucleotide, or combinations thereof.

The oligonucleotides of the present invention are for example consisting of 10 to 30, 12 to 25, or 14 to 20 nucleotides.

The oligonucleotide of the present invention is for example used in preventing and/or treating of wet age-related macular degeneration (AMD), dry AMD, diabetic retinopathy (DR), diabetic macular edema (DME), choroidal neovascularization of any type, proliferative vitreoretinopathy (PVR), primary open angle glaucoma (POAG), e.g., glaucoma (hypertensive and/or normotensive), glaucoma undergoing trabeculectomy (hypertensive and/or normotensive), normotensive or hypertensive glaucoma undergoing laser-based therapy and/or corneal diseases such as pterygium or keratoconus.

The present invention further relates to a pharmaceutical composition comprising an oligonucleotide of the present invention and a pharmaceutically acceptable excipient.

The oligonucleotide and the pharmaceutical composition, respectively, of the present invention are administered locally or systemically.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

DESCRIPTION OF FIGURES

FIG. 1A to 1C depict downregulation of TGF-beta2 mRNA in choroid and retina (A), optic nerve (B) and lens (C) after single intravitreal (IVT) injection of ISTH0036 to New Zealand White (NZW) rabbits.

FIGS. 2A and 2B show TGF-beta2 mRNA expression in retina and choroid tissues of the NZW rabbit after one or two IVT administration(s) of ISTH0036.

FIGS. 3A and 3B depict TGF-beta2 protein levels in vitreous humor of the NZW rabbit after one (FIG. 3A) or two (FIG. 3B) IVT administration(s) of ISTH0036.

FIGS. 4A and 4B depict the effect of ISTH0036 on bleb size and survival in an experimental mouse glaucoma filtration surgery model.

FIGS. 5A and 5B show the effect of ISTH0036 on collagen deposition in the bleb area in an experimental mouse glaucoma filtration surgery model.

FIG. 6A to 6D depict the effect of ISTH0036 on inflammation, FITC-positive area and ECM deposition in an experimental choroid neovascularization (CNV) mouse model. Results represent (FIG. 6A) the mean CD45 positive area/total lesion area (n=10), (FIG. 6B) the mean FITC positive area/total lesion area, (FIG. 6C) the mean Col1 positive area/total lesion area and (FIG. 6D) the mean SR positive area/total lesion area after single IVT injection of saline/vehicle control, C3_ASPH_0047 scrambled control oligonucleotide or ISTH0036 in an experimental CNV mouse model.

FIG. 7 shows a time-dependent decrease of CNV lesions induced by laser burns in mice.

FIG. 8 shows a pharmacokinetic profile in vitreous humor and biodistribution in ocular tissues of New Zealand White rabbits after IVT injection of ISTH0036. ISTH0036 (191 μg; 50 μL, in order to achieve an approximate concentration of 30 μM in vitreous humor) were administered via IVT injection in both eyes of NZW rabbits. Two animals (i.e., 4 eyes) were sacrificed at each indicated time point (FIG. 8).

FIG. 9 depicts a biodistribution profile in selected ocular tissues of NZW rabbits following one or two IVT administration(s) of ISTH0036. Mean ISTH0036 tissue concentrations in retina and choroid, ciliary body and iris, optic nerve head and sclera after one IVT (solid line) or two (dotted line) injection(s) at 200 μg/eye to NZW rabbits (n=4 eyes from 2 animals). Tissue samples were collected at indicated days after the first IVT administration. ISTH0036 was administered on Day 1 (single administration) or Days 1 and 56 (two administrations).

FIGS. 10A and 10B show individual intraocular pressure (IOP) course post GFS (FIG. 10A) and mean IOP per Dose Level (FIG. 10B). Patients treated with doses intended to result in intravitreal concentrations of 0.3, 1, 3 or 10 μM ISTH0036 in a single IVT injection at time point of surgery, in combination with mitomycin C, postoperative manipulations permitted, such as suture lysis, massage, e.g. bulbus massage, 5-FU administration. IOP was measured in both eyes after 1.5 (Day 43) and 3 months (Day 85) after surgery with Goldmann applanation tonometer. Fluoresein and anaesthetic agents were the same at all measurements. Two consecutive measurements were made for each eye and if the measurements differ by more than 2 mmHG a third measurement was made.

FIG. 11 depicts vascular leakage area corrected for presence of "0" values (37% of lowest values are excluded) and outliers. Data are expressed as mean±SEM.

FIG. 12 shows median ISTH0036 tissue concentrations after one injection on Day 1 (black straight line) or two injections on Days 1 and 57 (black dotted line) at 100 μg/eye in retina, choroid, ciliary body, optic nerve head, lens and kidney cortex. Samples were collected on Days 29, 57, 85 and 113 after the first intraocular administration from Cynomolgus monkey (n=4 eyes or kidney cortex samples from 2 animals).

FIG. 13 depicts dose-dependent biodistribution of ISTH0036 in selected ocular tissues and kidney (cortex).

FIG. 14 depicts time-dependent target (TGF-beta2 mRNA) engagement in selected ocular tissues.

FIG. 15 shows TGF-beta2 mRNA expression in ocular tissues of the Cynomolgus monkey 28 days after single IVT administrations of ISTH0036.

FIG. 16 depicts TGF-beta1, -beta2 and -beta3 protein concentration in aqueous and vitreous humor.

FIG. 17 shows long-term follow-up for individual intraocular pressure (IOP) course post GFS (see also FIGS. 10A and 10B). Patients treated with ISTH0036 doses resulting in concentrations of 3 or 10 μM with a single IVT injection at time point of surgery, in combination with mitomycin C still all managed to reside with their IOP≤11 mmHg at 26 weeks post surgery, indicative of a prolonged antifibrotic activity of ISTH0036.

DETAILED DESCRIPTION OF THE INVENTION

The present invention is directed to a TGF-beta oligonucleotide comprising or consisting a nucleic acid sequence of GACCAGATGCAGGA (SEQ ID No. 1; ISTH0036) or parts thereof comprising 1 to 4 modified nucleotides at the 3'-end and/or 5'-end of the oligonucleotide for use alone or in combination with an active agent in preventing and/or treating of an ophthalmic disease such as wet age-related macular degeneration (AMD), dry AMD, diabetic retinopathy (DR), diabetic macular edema (DME), choroidal neovascularization of any type, proliferative vitreoretinopathy (PVR), primary open angle glaucoma (POAG), e.g., normotensive glaucoma undergoing trabeculectomy, hypertensive (open-angle or closed-angle) glaucoma undergoing trabeculectomy, normotensive or hypertensive glaucoma undergoing laser-based therapy, secondary cataract (PCO) and/or corneal diseases (e.g., Pterygium, Keratoconus). For example age-related macular degeneration (AMD) is the primary cause of blindness in industrialized countries Loss of visual acuity typically results from progressive degeneration of the photoreceptors, retinal pigment epithelium (RPE) and choriocapillaris (geographic atrophy). The advanced form of the disease is characterized by pathologic choroidal neovascularization (CNV) under the retina. When neovascularization occurs, there is commensurate accumulation of fluid, hemorrhage and lipid exudation within the macula that can culminate in fibrosis referred to as disciform scar. The disease nearly always begins as the non-neovascular or dry form of AMD and may progress to the geographic atrophy or the neovascular (wet) form in one or both eyes (Pirtella Nunes et al., 2014). Diabetic macular edema (DME) is one of the ocular manifestations of diabetic retinopathy. The intercellular fluid comes from leaking microaneurisms or from diffuse capillary incompetence. Similar to AMD is DME an ocular disease that cause blindness (Lim et al., 2014). Proliferative vascular retinopathy (PVR) is a disease caused by the formation of fibrotic tissue on the detached retina, which reduces the flexibility of the retina and may potentially make it difficult to reattach to the retina (Kroll et al., 2007). The RPE cell is the most critical contributor to the development of fibrous tissue on the retina.

In particular, the oligonucleotide of SEQ ID No. 1 (e.g., ISTH0036) is used in the treatment of an ophthalmic disease such as mentioned above in an advanced disease stage. An advanced disease stage for example in DME or wet AMD is determined as a stage when neovascularization has occurred and vascular leakage is present, resulting in reduction of visual acuity and increased central foveal thickness.

An example of such TGF-beta oligonucleotide is ISTH0036 (former ASPH_0036) which consists of SEQ ID No. 1, wherein all 3'-5' linkages are modified to phosphorothioates and the oligonucleotide includes three locked nucleotides (LNAs) at the 3' and 5' ends (3+3 LNA-modified gapmer). ISTH0036 has the sequence GACCA-GATGCAGGA, wherein LNA modified nucleotides are indicated in bold letters (SEQ ID No. 2). The chemical name of ISTH0036 is 2'-O-,4'-C-methylene-P-thioguanylyl-(3'→5')-
2'-O-,4'-C-methylene-P-thioadenylyl-(3'→5')-
2'-O-,4'-C-methylene-5-methyl-P-thiocytidyl-(3'→5')-
2'-deoxy-P-thiocytidyl-(3'→5')-
2'-deoxy-P-thioadenylyl-(3'→5')-
2'-deoxy-P-thioguanylyl-(3'→5')-
2'-deoxy-P-thioadenylyl-(3'→5')-
2'-deoxy-P-thiothymidylyl-(3'→5')-
2'-deoxy-P-thioguanylyl-(3'→5')-
2'-deoxy-P-thiocytidyl-(3'→5')-
2'-deoxy-P-thioadenylyl-(3'→5')-
2'-O-,4'-C-methylene-P-thioguanylyl-(3'→5)-
2'-O-,4'-C-methylene-P-thioguanylyl-(3'→5)-
2'-O-,4'-C-methylene-adenosine tridecasodium salt.

Throughout this specification and the claims, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

Oligonucleotides of the present invention are highly efficient in reducing or inhibiting of scarring, in reducing or inhibiting of fibrotic closure of the trabeculectomy canal, in reducing or inhibiting of epithelial-to-mesenchymal transition of the trabecular meshwork and/or in providing of protecting activity of the optic nerve for example the optic nerve head. The oligonucleotide of the present invention comprises or consists of SEQ ID No. 1 (GACCA-GATGCAGGA) or parts thereof, wherein 1 to 4, i.e., 1, 2, 3, or 4 nucleotides at the 3'-end and/or 1, 2, 3, or 4 nucleotides at the 5'-end are modified at a base, a sugar and/or a phosphate. Parts of the oligonucleotide of SEQ ID No. 1 comprise for example at least 5 nucleotides having 1, 2, 3, or 4 modified nucleotides at the 3'-end or the 5'-end. An example of a phosphate modification is the phosphorothioate, wherein one or more (e.g., 10%, 20%, 30% 40% 50% 60%, 70%, 80%, 90% or 100%, i.e., all) of the 3'-5' linkages of an oligonucleotide are modified to phosphorothioates. Modifications at the sugar and/or base of the oligonucleotide are for example LNA, ENA; polyalkylene oxide-, 2'-fluoro-, 2'-O-methoxy-, and 2'-O-methyl-modified nucleotides. Oligonucleotides of the present invention comprise one or more of the same or different modifications. Oligonucleotides comprise for example 3'-, 5'-phosphorothioate linkages and LNA modified nucleotides at the 3'- and/or 5'-end of the oligonucleotide.

An oligonucleotide of the present invention consists of about 10 to about 30, about 12 to about 25, or about 14 to about 20 nucleotides. For example an oligonucleotide consists of about 10, 11, 12, 13, 14, 15, 16, 17, 18, 19, 20, 21, 22, 23, 24, 25, 26, 27, 28, 29 or 30 nucleotides.

Oligonucleotides of the present invention are for example characterized by
  a potent and highly selective TGF-beta2 suppression (e.g., in vitro and in vivo),
  high ocular tissue uptake rate and distribution,
  long-lasting target suppression, e.g., in ocular tissue, dosing monthly, every two, three, six, nine or twelve months,
  potent antifibrotic, anti-angiogenic and anti-EMT effect, and
  safe repeat dose administration, respectively.

A long lasting effect is for example detectable on the IOP level. Oligonucleotides of the present invention such as ISTH0036 keep the IOP level persistently below 10 mmHg for up to 12 weeks, 24 weeks, 9 months, or one year.

The oligonucleotides of the present invention are characterized by a rapid initial clearance rate for example from the vitreous humor which is associated with rapid and pronounced ocular tissue distribution. The initial distribution rate is for example 1, 2, 3, 4, 5, 6, or 7 h.

Oligonucleotides of the present invention are administered alone, for example dissolved in a saline solution of e.g., 0.7 or 0.9%, or in combination with an active agent, wherein the oligonucleotide and the active agent are administered at the same time or at different time points, e.g., before a surgery and/or the administration of an active agent, or after a surgery and/or the administration of an active agent. The time period between the administration of an oligonucleotide of the present invention such as ISTH0036 and the surgery or an active agent is for example a few hours such as 1, 2, 3, 4, 5, 6, 7, 8, 9, 10, 11, 12, 13, 14, 15, 16, 17, 18, 19, or 20 h, or some days such as 1 d, 2 d, 3 d, 4 d, 5 d, 6 d, or 7 d, or 1.5 weeks, 2 weeks, 3 weeks, 4 weeks, 5 weeks or 6 weeks.

The active agent is for example a cytostatic, an anti-VEGF agent, an anti-PDGF agent, an anti-complement agent, an anti-neovascular agent, an anti-ROCK agent and/or an antifibrotic agent. The active agent is for example selected from the group consisting of mitomycin C and an anti-VEGF treatment such as ranibizumab, bevacizumab (Avastin) or aflibercept, or combinations thereof, or other anti-VEGF agent (e.g., anti-VEGF receptor 2 antibody). Other agents may include PDGF—(such as Fovista™) or ROCK—(such as Rhopressa™) or complement-targeting agents (such as lampalizumab) or agents targeting other pathways related to ocular disease. The administration of an oligonucleotide of the present invention into the eye may be combined with postoperative manipulations such as needling e.g. needling alone, needling in combination with MMC, needling in combination with 5-FU administration, suture lysis, massage e.g. bulbus massage, 5-FU administration, anti-glaucoma medication or any combination thereof e.g., at time point of surgery; alternatively, surgery is repeated. An oligonucleotide of the present invention such as ISTH0036 is for example administered in combination with ant-VEFG for use in treating refractory wet AMD and DME, respectively.

The oligonucleotide of the present invention is used for example in a range of 0.01 to 50 µM, 0.02 to 45 µM, 0.03 to 40 µM, 0.05 µM to 35 µM, 0.08 µM to 30 µM, 0.1 to 25 µM, 0.3 to 20 µM, 0.5 to 15 µM, 0.8 to 12 µM, 0.9 to 10 µM, 1 to 9 µM, 3 to 8 µM, or 5 to 6 µM. For example the oligonucleotide may be used in a concentration of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 12, 15, 18, 20, 22, 25, 28, 30, 40 or 50 µM.

The present invention further refers to a pharmaceutical composition comprising an oligonucleotide of the present invention and a pharmaceutically acceptable excipient. Pharmaceutically acceptable excipients include, but are not limited to, a binding agent (e.g. pregelatinized maize starch, polyvinylpyrrolidone or hydroxypropyl methylcellulose, etc.); a filler (e.g. lactose and other sugars, microcrystalline cellulose, pectin, gelatin, calcium sulfate, ethyl cellulose, polyacrylates or calcium hydrogen phosphate, etc.); a lubricant (e.g., magnesium stearate, talcum, silica, colloidal silicon dioxide, stearic acid, metallic stearates, hydrogenated vegetable oils, corn starch, polyethylene glycols, sodium benzoate, sodium acetate, etc.); a disintegrate (e.g., starch, sodium starch glycolate, etc.); or a wetting agent (e.g., sodium lauryl sulphate, etc.). The pharmaceutical composition may further comprise an active agent as previously mentioned.

The oligonucleotide and/or the pharmaceutical composition are for example produced in a sustained release formulation of the oligonucleotide, wherein the oligonucleotide is released from the administration of the oligonucleotide over a defined time period or in a retard formulation, wherein the oligonucleotide is released after a defined time period. The oligonucleotide and/or the pharmaceutical composition is formulated as dosage unit in form of capsules, tablets, pills, eye drops, eye ointment and as solution for suprachoroidal, intrascleral, sub-Tenon's, subconjunctival, intracameral or intravitreal injection.

The oligonucleotide and/or the pharmaceutical composition of the present invention is administered locally or systemically for example it can be administered intranasally, intraocular, e.g., intracamerally, intravitreally, intraretinal, subretinal, subconjunctival, intravenous, orally, or subcutaneously.

The administration of an oligonucleotide of the present invention leads for example to accumulation of the drug in ocular tissue. In ocular administration highest concentrations of oligonucleotides of the present invention such as an oligonucleotide of SEQ ID No. 1 is measured in ciliary body, iris, choroid, retina and optic nerve head. The oligonucleotide of the present invention such as the oligonucleotide of SEQ ID No. 1 is for example characterized by long-lasting ocular tissue distribution, following for example intravitreal or intracameral administration which results in rapid and/or long-lasting (e.g., up to 1-4 months) sequence-specific downregulation of for example TGF-beta1, -2 and/or -3 mRNA in retina and choroid, optic nerve, lens and/or vitreous humor.

Several in vivo pharmacology studies performed with an oligonucleotide such as the oligonucleotide of SEQ ID No. 1 upon intra-ocular injection(s) in mice for example demonstrated significant sequence-specific increase in bleb size and/or in survival post-operative filtration surgery (glaucoma filtration surgery model), marked decrease in the level of neoangiogenesis and/or in blood vessel leakage in choroidal neovascularization model post laser-induced Bruch's membrane burns. In addition, oligonucleotides of the present invention show anti-fibrotic effects in these models.

Further, oligonucleotides such as the oligonucleotide of SEQ ID No. 1 are characterized by high metabolic stability for example in serum and/or in the eye, e.g., the vitreous humor, and/or high protein binding (e.g., >80%, >85%, >90% or >95%) across species. An oligonucleotide of the present invention remains for example stable and effective in ophthalmic tissue or humor such as vitreous humor for 30 to 120 days, 40 to 110 days, 50 to 100 days, 60 to 90 days or 90 to 120 days, e.g., 30, 35, 40, 45, 50, 55, 60, 65, 70, 75, 80, 85, 90, 95, 100, 105, 110, 115 or 120 days.

The oligonucleotide or the pharmaceutical composition comprising such oligonucleotide of the present invention are for use in a method of preventing and/or treating for example of wet age-related macular degeneration (AMD), dry AMD, diabetic retinopathy (DR), diabetic macular edema (DME), choroidal neovascularization of any type, proliferative vitreoretinopathy (PVR), primary open angle glaucoma (POAG), e.g., hypertensive and/or normotensive glaucoma undergoing trabeculectomy, hypertensive and/or normotensive glaucoma, hypertensive and/or normotensive glaucoma undergoing laser-based therapy, secondary cataract (PCO) and/or corneal diseases such as pterygium or keratoconus including any advanced form of these diseases. An oligonucleotide of the present invention such as ISTH0036 for example inhibits choroidal neovascularization, inhibits vascular leakage, and/or inhibits fibrosis The oligonucleotide or the pharmaceutical composition for use in preventing and/or treating of one of these diseases is administered one or more times, e.g., 1× per week, 1× or 2× per month, 1× or 2× every other month, 1× or 2× every 3, 4 or 5 months, 1× every six months or 1× per year, or after 30 to 120 days, 40 to 110 days, 50 to 100 days, 60 to 90 days or 90 to 120 days.

In advanced stage glaucoma trabeculectomy is the standard surgical intervention to reduce intraocular pressure in subjects not responding sufficiently anymore to pressure-lowering medications. Yet, scarring of the surgically opened canal ("bleb-closure") often abolishes the effect of trabeculectomy (despite the intraoperative use of Mitomycin C to prevent this) and the surgical intervention itself does not block core glaucoma pathophysiologic processes. Importantly, TGF-beta2 plays a distinct role in the fibrotic process of bleb closure. Consequently, blocking the effect of TGF-beta2 by a selective antisense oligonucleotide (ASO) such as ISTH0036 in the context of trabeculectomy appears to be an attractive potential therapeutic concept to (1) prevent bleb closure, (2) block any key pathophysiology of TGF-beta2 in glaucoma progression (trabecular meshwork transformation with IOP-rise and optic nerve damage).

EXAMPLES

In the following examples for the use of oligonucleotides of the present invention are provided for a more detailed understanding of the present invention, wherein the present invention is not limited to these examples.

Example 1: Downregulation of TGF-Beta2 mRNA in Choroid and Retina (A), Optic Nerve (B) and Lens (C)

Target mRNA (TGF-beta2) expression was analyzed—after single IVT injection of ISTH0036 in both eyes (191 µg;

50 µL per eye, in order to achieve an approximate final test item concentration of 30 µM in the vitreous humor) of NZW rabbits—in choroid and retina (FIG. 1A), optic nerve (FIG. 1B) and lens (FIG. 1C). IVT injections were performed on day 0 and animals (2 animals per group) were sacrificed at the indicated times. All ocular tissues (both anterior and posterior) were dissected and immediately snap frozen for further analysis of target mRNA downregulation and tissue drug concentration. TGF-beta2 mRNA levels were quantified and normalized to corresponding GAPDH mRNA values. Data are represented as box plots, in which median values (line), upper and lower quartiles, and 90th and 10th percentiles are indicated. Both aqueous and vitreous humor, as well as anterior (cornea and lens) and posterior (iris and ciliary body-sampled together, choroid and retina-sampled together, sclera and optic nerve) ocular tissues were dissected for further analysis of target mRNA downregulation and drug tissue biodistribution (e.g., Example 8). As shown in FIG. 1A to 1C, TGF-beta2 mRNA downregulation (target engagement) was clearly demonstrated in choroid and retina, optic nerve and in the lens in a time-dependent manner. Within the same study, repeated (3) IVT administrations 2-week apart (Q2W×3, i.e. every second week three cycles)) were also evaluated and showed no further increase in target mRNA downregulation (data not shown).

Example 2: TGF-Beta2 mRNA Expression in Retina and Choroid Tissues of the NZW Rabbit after One or Two IVT Administration(s) of an Antisense Oligonucleotide of SEQ ID No. 1 (ISTH0036)

ISTH0036 (200 µg/50 µL) was administered in NZW rabbit eyes via a single (Day 1; FIG. 2A) or two (Days 1 and 56; FIG. 2B) IVT injection(s). The test item was injected in both eyes of the animals, 2 animals per time point were sacrificed on Days 14, 28, 56, 70, 84 96 and 112 of Group 2 and 2 animals on Day 70, 84, 96 and 112 of Group 3 (n=4 eyes). Retina and choroid were dissected and immediately snap frozen for further analysis of target mRNA downregulation. TGF-beta2 mRNA levels were quantified by bDNA assay and results were normalized to GAPDH values. Data are represented as box plots, in which median values (line), upper and lower quartiles, and min and max values are indicated. (*) p<0.05 compared to untreated (2-sided p values). Statistical significance was analyzed using non-parametric 2-independent samples Wilcoxon-Mann Whitney test.

Long-lasting and significant TGF-beta2 mRNA downregulation was observed in the retina and choroid until Day 112. Only on Day 70 after the IVT injection of ISTH0036, the target downregulation normalized to baseline level, for which no explanation exists and which might have been an outlier. Also shown in FIGS. 2A and 2B, no apparent additional effect of a second IVT injection on Day 56 was observed on the extent of downregulation of TGF-beta2 mRNA in the retina and choroid. Consistent with previous experiments (Example 1), significant and relevant target downregulation of TGF-beta2 mRNA was observed in lens tissue on Day 14 and Day 28 (data not shown). Later time points could not be analyzed in this study due to low quality of the tissue samples, which correlates with the appearance of lens findings in the ophthalmic examination.

Example 3: TGF-Beta2 Protein Levels In Vitreous Humor of the NZW Rabbit after One or Two IVT Administration(s) of an Antisense Oligonucleotide of SEQ ID No. 1 (ISTH0036)

ISTH0036 (200 µg/50 µL) was administered in NZW rabbit eyes via IVT injection. The test item was injected in both eyes of the animals. Vitreous humor was collected on the indicated Days (n=4 eyes) and immediately snap frozen for further analysis of TGF-beta2 protein concentration. Protein levels were determined by multiplex analysis. Data are represented as individual dot plots and median values (red lines) are indicated. (*) p<0.05 compared to untreated (2-sided p values). Statistical significance was analyzed using non-parametric 2-independent samples Wilcoxon-Mann Whitney test.

FIG. 3 shows long-lasting TGF-beta2 protein reduction (with return to baseline on Day 84) in the vitreous humor after a single IVT administration of ISTH0036, suggesting full target (protein) engagement on Days 56 and 70 after single IVT administration (FIG. 3A). The second ISTH0036 administration (on Day 56) caused sustained reduced protein expression levels up to Day 112 (although to a slightly lower extent; FIG. 3B). A long-lasting TGF-beta2 protein reduction was also observed in the aqueous humor (with return to baseline on Day 70) after single IVT administration of ISTH0036 (data not shown). Similar to TGF-beta2 levels in the vitreous humor, an apparent, but less pronounced and sustained additional effect with second IVT administration was seen.

Example 4

Effect of ISTH0036 on bleb size and survival in an experimental mouse glaucoma filtration surgery model C57BL/6J mice were used for a filtration surgery on both eyes, using a technique that has been described previously and that results in a filtering bleb (Seet et al., 2011). The bleb size was measured via digital photographs. Bleb survival was determined at the end of the study, while bleb failure was defined as the appearance of a scarred and flat bleb at two consecutive measurements. Mean bleb area (n=5) after single IVT (FIG. 4A) or intracameral (ICM) (FIG. 4B) injection of saline, C3_ASPH_0047 scrambled control (having the sequence CTATTACGACCGTTAGT, wherein LNA modified nucleotides are indicated in bold letters) or ISTH0036 of about 1 µg to mice after glaucoma filtration surgery (GFS) (performed on day 0). Injections were performed at the time of surgery, and repeated on day 14. Mean bleb size (expressed as µm$^2$) was measured via digital photographs at the indicated times.

As illustrated in 4A and 4B no significant differences were observed between the saline- and the scrambled control oligonucleotide-treated groups on bleb area and survival which strongly support sequence-dependent effects. In contrast, ISTH0036 was shown to induce a statistically significant increase in bleb area, as compared to saline- or control scrambled oligonucleotide-treated eyes. Analysis of bleb survival showed that all blebs in the saline- and control oligonucleotide-treated groups failed at Day 17, while the blebs treated with ISTH0036 failed at Day 19 (for IVT). Interestingly, following ICM administrations of about 1 µg of ISTH0036, a greater increase in bleb area, as compared to saline- or scrambled oligonucleotide-treated eyes (FIG. 4B); and in the saline- and the control oligonucleotide-treated groups, all blebs failed around Day 17, whereas 100% of the blebs survived after ISTH0036 treatment at day 27.

Example 5: Effect of ISTH0036 on Collagen Deposition in the Bleb Area in an Experimental Mouse Glaucoma Filtration Surgery Model Deposition of collagen was determined by measuring the percentage of the collagen positive area in the bleb area.

Polarized light was used to distinguish mature from immature collagen fibers. Mature collagen fibers appear bright yellow or orange, whereas immature collagen fibers appear green. Results represent the mean Sirius Red positive area (±SD; n=4) after IVT (FIG. 5A) or ICM (FIG. 5B) injection of saline, C3_ASPH_0047 scrambled control oligonucleotide or ISTH0036 to mice following glaucoma filtration surgery (GFS; performed on day 0). Injections of ISTH0036 were performed at the time of surgery, and repeated on day 14. Sirius Red positive area (expressed as %) was measured via digital photographs on day 28. Student's t-test was used to determine the significance of the differences between vehicle control and C3_ASPH_0047 or ISTH0036 (* $p<0.05$).

Analysis of the Sirius Red positive area in IVT and ICM injected mice showed that no differences in collagen deposition could be seen between saline- and C3_ASPH_0047 scrambled control oligonucleotide-treated eyes at day 28. In contrast, treatment with the ISTH0036 was able to significantly reduce the deposition of extracellular matrix, namely collagen, after IVT and ICM injection (FIGS. 5A and 5B).

Example 6: Effect of ISTH0036 on Inflammation, FITC-Positive Area and ECM Deposition in an Experimental CNV Mouse Model C57BL/6J mice were anesthetized and three laser burns were placed around the optic disk on the Bruch's membrane. Injections were performed immediately after laser surgery (Day 0) and on postoperative Day 14. Mice were sacrificed on postoperative Days 5, 14 and 28 after surgery. Results (indicative of extent of angiogenesis) are expressed as mean FITC-positive area (n=10 eyes, ±SD) after single IVT injection of saline (vehicle control), C3_ASPH_0047 (scrambled control oligonucleotide) or ISTH0036 (FIG. 6A to 6D). Student's t-test was used to determine the significance of the differences between vehicle control and C3_ASPH_0047 or ISTH0036 (* $p<0.05$).

Mice were divided in different groups (5 animals per group; both eyes treated). All injections were performed immediately after laser induction (D0) and on postoperative day 14. Mice were sacrificed on postoperative Day 5, 14 and 28 after surgery for further histological analysis. To analyze the effect on Day 5 on inflammatory cell infiltration in the CNV lesions, the choroids were dissected and histological staining to detect all leukocytes was performed. Analysis of the CD45 positive area/total spot area showed that no differences in inflammation could be seen between saline, C3_ASPH_0047 and ISTH0036 (FIG. 6A). For the investigation of the effect on angiogenesis, retrobulbar perfusion with 200 µl of fluorescein isothiocyanate (FITC)-conjugated dextran was performed on Day 14. As indicated in FIG. 6B, preliminary analysis of the FITC positive area/total spot area showed that no differences in angiogenesis could be seen between saline- and C3_ASPH_0047 scrambled control (sequence shown in Example 4) oligonucleotide-treated eyes at Day 14. In contrast, treatment with ISTH0036 (about 1 µg, leading to ~30 µM final concentration in vitreous humor) was able to significantly reduce the process of angiogenesis. Data about the analysis of collagen deposition by Sirius Red (SR) staining and collagen I (Col I) immunostaining show a significant decrease in ECM deposition after IVT treatment with ISTH0036 compared to saline or C3_ASPH_0047 scrambled control injection (FIGS. 6C and 6 D).

Example 7: Time-Dependent Decrease of CNV Lesions Induced by Laser Burns in Mice C57BL/6J mice were anesthetized and three laser burns were placed around the optic disk on the Bruch's membrane. Injections were performed immediately after laser surgery (Day 0) and on postoperative Day 14. The presence of CNV lesions at the indicated times was monitored in living animals, and results were expressed as percentage of CNV lesions in each treatment group (n=8-9, with 3 laser burns/eye). Aflibercept-treated group had lowest intercepts on Day 5 and Day 7 (vs non-treated group, Fisher's exact test, P=0.0077) and had statistically significant difference at Day 14 as compared to non-treated group (P=0.0415). ISTH0036-treated group had lowest intercepts on the follow-up day 10 (vs non-treated group, P 0.042; and vs C3_ASPH_0047 group, P=0.0095; sequence shown in Example 4) and Day 14 (vs non-treated group, P=0.0027; and vs C3_ASPH_0047 group, P=0.0037).

A significant beneficial effect of ISTH0036 on the progression of CNV pathology (FIG. 7) and vascular leakage (data not shown) was demonstrated, which was similar to the effect observed in aflibercept-treated mice. In addition, administration of ISTH0036 decreased fibrosis in the mouse CNV model as compared to scrambled control group (data not shown).

Example 8: Ocular Pharmacokinetic and Target Eye Tissue Distribution in the New Zealand White Rabbit (Intravitreal Administration)

ISTH0036 (191 µg; 50 µL, in order to achieve a calculated concentration of 30 µM in the vitreous humor) was injected in the vitreous humor (IVT injection) of New Zealand White (albino) rabbits. Injections were performed in both eyes of the rabbits, and animals (2 animals per group; n=4 eyes) were sacrificed at the indicated times. Both anterior (aqueous humor, cornea and lens) and posterior (vitreous humor, iris and ciliary body, choroid and retina, sclera and optic nerve) ocular tissues were dissected and immediately snap frozen for further analysis of tissue drug concentrations. As illustrated in FIG. 8, following single IVT administration, ISTH0036 shows a biphasic pharmacokinetic (PK) profile in vitreous humor, with rapid initial clearance ($T_{1/2}\alpha$~24 h) from the vitreous humor and only a limited, if any, transfer and delivery to anterior eye tissues (aqueous humor, lens and cornea; data not shown). Long half-life ($T_{1/2}\beta$ of several weeks) was observed in the vitreous humor. Fast and marked distribution of the test drug to the posterior tissues (choroid and retina, iris and ciliary body, optic nerve and sclera) was observed, with a $T_{MAX}$ of 24-48 h. The highest mean concentration (114 µg/g) of ISTH0036 was measured in the ciliary body and iris after 24 h of injection, followed by retina and choroid, optic nerve and sclera (30-40 µg/g). High drug concentrations in posterior eye tissues (especially in retina and choroid samples) were still observed 56 days after single IVT injection of ISTH0036 supporting the concept of very intermittent schedule of administration (e.g., every other month) in human patients.

Example 9: Drug Concentration in Selected Ocular Tissues of NZW Rabbits Following One or Two IVT Administration(s) of ISTH0036

ISTH0036 was intravitreally administered in NZW rabbits at a dose of 200 µg/eye/administration. As illustrated in FIG. 9 following IVT administration, ISTH0036 showed a long-lasting tissue distribution with a long terminal half-life. The highest mean concentration after single IVT administration was measured on Day 14 (first measurement after ISTH0036 administration) in the retina and choroid (45 µg/g) followed by ciliary body and iris, optic nerve and sclera (2-20 µg/g). High drug concentrations in posterior eye tissues were still observed 112 days after a single IVT injection of ISTH0036, for example 5.1 µg/g in choroid & retina tissue. When a second IVT administration was performed on Day 56, accumulation was evident in most of the examined ocular tissues. Mean concentrations, measured 14 days after first or second administration, increased in retina and choroid from single-dose concentration of approximately 45 to 51 µg/g after two doses, in ciliary body and iris from 19 to 45 µg/g, in optic nerve head from 3.5 to 5.2 µg/g, whereas in sclera no accumulation was observed (2.4 µg/g).

Example 10: Intraocular Pressure (IOP) Measurement

4×3 patients (cohorts 1 to 4) were treated with doses intended to result in intravitreal concentrations in the vitreous humor of 0.3, 1, 3 or 10 µM of a TGF-beta antisense oligonucleotide in a single IVT injection. TGF-beta antisense oligonucleotides of the present invention, e.g., ISTH0036 were reconstituted according to the following:

Cohort 1: 0.3 µM ISTH0036 (6.75 µg total dose)

6.75 mg drug product reconstituted in 5 ml 0.9% normal saline solution for injection. After mixing, 4.5 ml of solution were withdrawn and discarded. A further 4.5 ml of 0.9% normal saline solution for injection was added to achieve a final concentration of approximately 0.3 µM in the vitreous body, assuming a human vitreous humor volume of 4.5 ml.

Cohort 2: 1 µM ISTH0036 (22.5 µg total dose)

6.75 mg drug product reconstituted in 3 ml 0.9% normal saline solution for injection. After mixing, 2.5 ml of solution were withdrawn and discarded. A further 2 ml of 0.9% normal saline solution for injection were added to achieve a final concentration of approximately 1 µM in the vitreous body.

Cohort 3: 3 µM ISTH0036 (67.5 µg total dose)

6.75 mg drug product reconstituted in 2.5 ml 0.9% normal saline solution for injection. After mixing, 1.5 ml of solution were withdrawn and discarded. A further 1 ml of 0.9% normal saline solution for injection were added to achieve a final concentration of approximately 3 µM in the vitreous body.

Cohort 4: 10 µM ISTH0036 (225 µg total dose)

6.75 mg drug product reconstituted in 1.5 ml 0.9% normal saline solution for injection equivalent to a final concentration of approximately 10 µM in the vitreous body.

The TGF-beta antisense oligonucleotides was administered as an intravitreal injection on Day 1 (during surgery, at the end of the trabeculectomy surgical procedure, after topical mitomycin C (MMC) administration). 50 µl of the reconstituted ISTH0036 was injected into the vitreous humor of the target eye. IOP was measured in both eyes using the Goldmann applanation tonometer. The IOP measurements was done in the sitting position. The fluorescein and anesthetic agent were the same at each measurement. Two consecutive measurements were made for each eye and if the measurements differed by more than 2 mmHg a third measurement was done. The median of all measurements was considered the IOP for that eye.

FIG. 10A shows the results, i.e., all dose level 3 and 4 patients remain consistently with their IOP values below the for MMC-only expected zone (IOP ~10-12 mmHg, derived from large, randomized ph III trials for MMC) in a mean range of 6-8 mmHg (FIG. 10B).

Example 11: Dose Dependent Effect of ISTH0036 in Combination with Aflibercept on Choroidal Neovascularization and Collagen Deposition The growth of subretinal blood vessels was recruited from the choroid by perforating Bruch's membrane using diode laser. Immediately after the lasering unilateral intravitreal (IVT) administrations of scramble control antisense oligonucleotide (C3_ASPH_0047), ISTH0036 or aflibercept (Eylea, VEGF-TRAP) were performed (day 0). ISTH0036 was administered IVT two days before the lasering (day −2) only when combined with aflibercept. Scrambled control antisense oligonucleotide was dosed at 1 µg (leading to a calculated initial $C_0$ ~30 iµM concentration in vitreous humor), ISTH0036 was dosed at 0.01, 0.1 and 1 µg/eye (leading to a calculated initial $C_0$ ~0.3, 3 and 30 iµM concentration in vitreous humor, respectively). The dose of aflibercept was 4 µg/eye. The control group received 0.9% NaCl solution as IVT injection. The contralateral eye of all animals remained untouched (no lasering and no IVT injection). The mice were examined by in vivo imaging (fluorescein angiography (FA) and spectral domain optical coherence tomography (SD-OCT)) on day 0 (prior and after the laser application), day 5, day 10 and day 14. At the end of the study (follow-up day 28) the mice were transcardially perfused with a fixative and choroidal flat-mounts were prepared and immunostained against collagen 1a.

To compare the effect of treatment on CNV, the presence of CNV lesions was graded from OCT, FA choroidal and FA retinal images acquired on the follow-up day 0, day 5, day 10 and day 14. The data were expressed as percentage of number of already formed CNVs out of the total number of lasered spots (CNV induction sites) at a given measurement time-point in each treatment group (Table 1). IVT administered combination therapy of 4 µg of aflibercept with 0.1 µg of ISTH0036 significantly reduced the presence of CNV in the mouse model.

TABLE 1

CNV induction and presence of CNV lesions at given follow-up time points in different treatment groups.

| Group | CNV induction (%) Day 0 | CNV lesions (%) Day 5 | Day 10 | Day 14 |
|---|---|---|---|---|
| Scrambled control | 96.6 | 60.0 | 48.3## | 43.3 |
| ISTH0036, 0.01 µg | 100.0 | 60.0 | 45.0 | 35.0 |
| ISTH0036, 0.1 µg | 100.0 | 72.2 | 61.1 | 40.7 |
| ISTH0036, 1 µg | 96.3 | 79.6 | 66.6 | 51.8 |
| Aflibercept, 4 µg | 90.0 | 50.0* | 35.8# | 35.0 |
| ISTH0036, 0.1 µg + Aflibercept, 4 µg | 96.9 | 40.9** | 36.3### | 28.7§ |
| Vehicle (0.9% NaCl) | 100 | 73.3 | 68.3 | 60.0 |

CNV induction (day 0) is presented as percentage of laser spots with successful damage to Bruch's membrane out of all laser spots. CNV lesions at the follow-up time points is presented as percentage of already formed CNVs out of all successful laser points. The successful damage of Bruch's membrane was verified on day 0. All values are expressed as percentages (already formed CNVs/all lasered spots × 100).
*vs Vehicle group, Chi-square test, P = 0.0254;
**vs Vehicle group, Chi-square test, P = 0.0019;
vs Vehicle group, Chi-square test, P = 0.0027;
vs Vehicle group, Chi-square test, P = 0.047;
vs Vehicle group, Chi-square test, P = 0.0075;
§vs Vehicle group, Chi-square test, P = 0.0214.

FIG. 11 shows the results on the vascular leakage area corrected for presence of "0" values (37% of lowest values are excluded) and outliers. The vascular leakage area was derived from the 14-day FA images that were taken from retinal level. The vascular leakage was reduced in ISTH0036 treated eyes, already at the lowest tested dose of 0.01 µg/eye. The effect was comparable to aflibercept. The combination of ISTH0036 and aflibercept did not further reduce vascular leakage in this mouse model.

Example 12: Time-Dependent Biodistribution of ISTH0036 in Selected Ocular Tissues and Kidney (Cortex) of the Cynomolgus Monkey The time-dependent ocular tissue biodistribution of ISTH0036 was determined in Cynomolgus monkey following a single (Day 1) or two (Day 1 and Day 57) IVT administration(s) of 100 µg eye (calculated initial concentration in the vitreous humor $C_0$ ~10 µM) to both eyes. In addition, systemic exposure after intraocular injection was studied by measuring ISTH0036 concentration in kidney cortex of the animals. The ocular tissue and kidney cortex samples were collected on Day 29, 57, 85 and 113. Ocular tissues (retina, choroid, lens, optic nerve head and ciliary body) as well as kidney cortex samples were dissected and immediately frozen and stored in a deep freezer (below −70° C.) for further analysis of drug concentrations.

As illustrated in FIG. 12, following a single IVT administration, time-dependent drug distribution was observed in the examined posterior eye tissues. ISTH0036 showed a long-lasting tissue distribution with a slow elimination rate. The highest ISTH0036 concentrations were measured in the retina after the second administration (Day 85: 4 µg/g) followed by choroid, ciliary body, and optic nerve head (1-3 µg/g). High median drug concentrations in posterior eye tissues were still observed 28 days after the first or second IVT injection of ISTH0036, for example 1.9 µg/g (Day 57) and 2.5 µg/g (Day 113), respectively in the retina tissue.

Accumulation was evident in all of the examined ocular tissues with the second administration of ISTH0036 (on Day 57). Median concentrations, measured 28 days after first or second administration, increased in retina from single-dose concentration of approximately 2.5 to 4.0 µg/g after two doses, in choroid from 1.4 to 3.0 µg/g, in ciliary body from 1.6 to 2.7 µg/g and in optic nerve head from 0.5 to 1.4 µg/g as shown in FIG. 12. As previously seen in the rabbit, median drug concentrations in the lens and kidney cortex were low (<100 ng/g) after IVT injection.

Example 13: Dose-Dependent Biodistribution of ISTH0036 in Selected Ocular Tissues and Kidney (Cortex)

The dose-dependent ocular tissue biodistribution was determined in Cynomolgus monkey following a single (Day 1) IVT administration of 30, 100 or 300 µg ISTH0036/eye (calculated initial concentration in the vitreous humor $C_0$ ~3, 10 or 30 µM, respectively) to both eyes. In addition, systemic exposure after intraocular injection was studied by measuring ISTH0036 concentration in the right and left kidney cortex of the animals. The ocular tissue and kidney cortex samples were collected on Day 29.

Following a single IVT administration, a proportional drug distribution was observed in the examined eye tissues. Similar concentrations were reached in the retina, choroid and ciliary body as shown in FIG. 13. The median drug concentrations in the lens and kidney cortex were below <1 µg/g after the highest 300 µg/eye dose.

Example 14: Time-Dependent Target (TGF-Beta2 mRNA) Engagement in Selected Ocular Tissues The time-dependent target downregulation in ocular tissues was determined in Cynomolgus monkey following one or two IVT administration(s) of 100 µg ISTH0036/eye (calculated initial concentration in the vitreous humor $C_0$ ~10 µM) to both eyes. TGF-beta2 mRNA expression in retina, choroid, lens, optic nerve head and ciliary body samples as well as in kidney cortex was analyzed.

As shown in FIG. 14, long-lasting and significant TGF-beta2 mRNA downregulation was observed in the retina and lens until Day 113. Only a trend of TGF-beta2 mRNA target downregulation was observed in the optic nerve head when ISTH0036 was injected once on Day 1 or twice on Days 1 and 57. Similar results were previously seen in experiments in the rabbit. An apparent additional effect of the second IVT injection on Day 57 was observed in the retina and optic nerve head, whereas no target downregulation was observed in choroid, ciliary body and kidney tissue.

Example 15: Dose-Dependent Target (TGF-Beta2) Engagement in Selected Ocular Tissues The dose-dependent target downregulation in ocular tissues was determined in Cynomolgus monkey following a single IVT administration of different doses of ISTH0036.

As shown in FIG. 15, a strong dose-dependent target engagement (TGF-ß2 mRNA downregulation) in the lens and retina and to a lesser extend in optic nerve head was observed on Day 29 after ISTH0036 administration. Significant ($p<0.05$) decrease in TGF-beta2 mRNA levels was observed upon IVT administration of 100 and 300 µg ISTH0036 in retina and lens tissue. No target downregulation was observed in choroid, ciliary body or kidney tissues (data not shown).

Example 16: TGF-Beta1, -Beta2 and -Beta3 Protein Concentration in Aqueous and Vitreous Humor The protein expression of TGF-beta1, -beta2 and -beta3 in aqueous and vitreous humor of ISTH0036-treated Cynomolgus monkey was determined. In the time-dependency experiment, animals were treated with 100 µg/eye ISTH0036 on Day 1 and Day 57 and protein expression was determined on Days 29, 57, 85 and 113. In the dose-dependency experiment, humor samples were analyzed 28 days after a single IVT administration at indicated doses of ISTH0036.

As shown in FIG. 16, TGF-beta2 protein concentration decreased rapidly in the vitreous humor and this effect was long-lasting, up to the last day of measurement (Day 113). A minor additional effect of the second, Day 57, IVT administration was observed on Day 85. The TGF-beta2 protein concentration in the aqueous humor was almost 3-fold lower than in the vitreous humor and did not change upon ISTH0036 treatment. TGF-beta1 or TGF-beta3 protein concentrations were mostly below the detection limit (<10 pg/mL) in both vitreous and aqueous humor.

Example 17: Intraocular Pressure (IOP) at Week 26 in Humans—Testing Longterm Effects 4×3 patients (cohorts 1 to 4) were treated with doses intended to result in intravitreal concentrations in the vitreous humor of 0.3, 1, 3 or 10 µM of a TGF-beta antisense oligonucleotide in a single IVT injection. The TGF-beta antisense oligonucleotides ISTH0036 was administered as an intravitreal injection on Day 1 (during surgery, at the end of the trabeculectomy surgical procedure, after topical mitomycin C (MMC) administration).

In the longterm follow-up of patients depicted in FIGS. 10A and 10B IOP values at week 26 and 52 were also analyzed. DL3 and −4 treated patients all remained with their IOP up to Week 26 at or below 11 mmHg, while DL1 and DL2 patients mostly exceeded this value already at week 26. The results for ISTH0036 are shown in FIG. 17.

The invention claimed is:

1. A method of preventing or treating:
   i. dry AMD which is classified as an intermediate and/or drusen maculopathy, complete or incomplete retinal pigment epithelium (RPE), and outer retinal atrophy, or
   ii. geographic atrophy associated with late-stage AMD, or
   iii. wet AMD comprising macular neovascularization and new vessel formation below the RPE (Type 1) within the subretinal space (Type 2), retino-choroidal anastomosis (Type 3), branching vascular networks and polyp formation, or
   iv. diabetic macular edema (DME) comprising fluid accumulation in the center, presence of hard exudates, microaneurysms and intraretinal cystoid spaces due to diabetic metabolic syndrome, or
   v. choroidal neovascularization of any type, or
   vi. normotensive or hypertensive glaucoma, or
   vii. normotensive or hypertensive glaucoma undergoing trabeculectomy, or
   viii. dry eye due to laser-based therapy,
   said method comprising administering an oligonucleotide comprising a nucleic acid sequence of SEQ ID No. 1 (GACCAGATGCAGGA) or parts thereof:

wherein 1 to 4 nucleotides at the 3'-end and/or at the 5'-end of the oligonucleotide are modified at a base, a sugar and/or a phosphate; and wherein the oligonucleotide is administered in combination with at least one active agent and wherein said active agent is a cytostatic, an anti-VEGF agent, an anti-PDGF agent, an anti-complement agent, an anti- ROCK agent, an anti-neovascular agent, an antifibrotic agent, or an agent reducing or inhibiting neuroretinal decay.

2. The method of claim 1, wherein the modification of the administered oligonucleotide is LNA, ENA; polyalkylene oxide-, 2'-fluoro-, 2'-O-methoxy-, and 2'-O-methyl-modified nucleotide, or combinations thereof.

3. The method of claim 1, wherein said oligonucleotide consists of 10 to 30 nucleotides.

4. The method of claim 1, wherein said oligonucleotide reduces or inhibits epithelial-to-mesenchymal transition of the trabecular meshwork and/or protects activity of the optic nerve.

5. The method of claim 1, wherein at least one active agent is mitomycin C, ranibizumab, bevacizumab, aflibercept, or combinations thereof.

6. The method of claim 1, wherein the oligonucleotide is in a concentration of at least 0.01 µM.

7. The method of claim 6, wherein the oligonucleotide is in a concentration range of 0.01 to 50 µM.

8. The method of claim 1, wherein the oligonucleotide remains in ophthalmic tissue or humor for 30 to 120 days.

9. The method of claim 8, wherein the ophthalmic tissue or compound is selected from the group consisting of choroid/retina, optic nerve, ciliary body/iris, sclera, lens, cornea and/or vitreous humor.

10. A method of preventing or treating dry or wet AMD, diabetic macular edema (DME), choroidal neovascularization of any type, normotensive or hypertensive glaucoma, normotensive or hypertensive glaucoma undergoing trabeculectomy or dry eye due to laser-based therapy by administering a pharmaceutical composition comprising an oligonucleotide comprising a nucleic acid sequence of SEQ ID No. 1 (GACCAGATGCAGGA) or parts thereof:

wherein 1 to 4 nucleotides at the 3'-end and/or at the 5'-end of the oligonucleotide are modified at a base, a sugar and/or a phosphate and a pharmaceutically acceptable excipient; and wherein the oligonucleotide is administered in combination with at least one active agent and wherein said active agent is a cytostatic, an anti-VEGF agent, an anti-PDGF agent, an anti-complement agent, an anti-ROCK agent, an anti-neovascular agent, an antifibrotic agent, or an agent reducing or inhibiting neuroretinal decay.

11. The method of claim 1 wherein said oligonucleotide is locally or systemically administered.

12. The method of claim 10, wherein said pharmaceutical composition is locally or systemically administered.

13. The method of claim 1, wherein the oligonucleotide remains in ophthalmic tissue or humor for 90 to 120 days.

14. The method of claim 1, wherein the oligonucleotide is in a concentration of at least 10 µM.

15. The method of claim 14, wherein the oligonucleotide is in a concentration range of 5 to 6 µM.

16. The method of claim 1, said oligonucleotide consisting of 14 to 20 nucleotides.

17. The method of claim 10, wherein at least one active agent is mitomycin C, ranibizumab, bevacizumab, aflibercept, or combinations thereof.

18. The method of claim 1, wherein the wet AMD is Polypoidal Choroidal Vasculopathy (PCV).

\* \* \* \* \*

```
                    SEQUENCE LISTING

<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: TGF-beta oligonucleotide

<400> SEQUENCE: 1
gaccagatgc agga                                                     14

<210> SEQ ID NO 2
<211> LENGTH: 14
<212> TYPE: DNA
<213> ORGANISM: Artificial Sequence
<220> FEATURE:
<223> OTHER INFORMATION: LNA modified TGF-beta oligonucleotide
<220> FEATURE:
<221> NAME/KEY: modified_base
<222> LOCATION: (1)..(2)
<223> OTHER INFORMATION: LNA modified base
<220> FEATURE:
<221> NAME/KEY: modified_base
<222> LOCATION: (12)..(14)
<223> OTHER INFORMATION: LNA modified base

<400> SEQUENCE: 2
gaccagatgc agga                                                     14

<210> SEQ ID NO 3
<211> LENGTH: 17
<212> TYPE: DNA
<213> ORGANISM: Artificial Sequence
<220> FEATURE:
<223> OTHER INFORMATION: control sequence

<400> SEQUENCE: 3
ctattacgac cgttagt                                                  17
```